US012708895B2

(12) United States Patent
Iitsuka et al.

(10) Patent No.: US 12,708,895 B2
(45) Date of Patent: Aug. 18, 2026

(54) CATALYST FOR PRODUCTION OF CARBOXYLIC ACID ESTER, METHOD FOR PRODUCING CATALYST FOR PRODUCTION OF CARBOXYLIC ACID ESTER, AND METHOD FOR PRODUCING CARBOXYLIC ACID ESTER

(71) Applicant: ASAHI KASEI KABUSHIKI KAISHA, Tokyo (JP)

(72) Inventors: Chihiro Iitsuka, Tokyo (JP); Dai Nagata, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 686 days.

(21) Appl. No.: 17/802,610

(22) PCT Filed: Feb. 25, 2021

(86) PCT No.: PCT/JP2021/007189
§ 371 (c)(1),
(2) Date: Aug. 26, 2022

(87) PCT Pub. No.: WO2021/172466
PCT Pub. Date: Sep. 2, 2021

(65) Prior Publication Data

US 2023/0146477 A1 May 11, 2023

(30) Foreign Application Priority Data

Feb. 28, 2020 (JP) ................................ 2020-033203

(51) Int. Cl.

| | |
|---|---|
| ***B01J 23/02*** | (2006.01) |
| ***B01J 23/89*** | (2006.01) |
| ***B01J 35/30*** | (2024.01) |
| ***B01J 35/40*** | (2024.01) |
| ***B01J 35/52*** | (2024.01) |
| ***B01J 37/00*** | (2006.01) |
| ***B01J 37/04*** | (2006.01) |
| ***B01J 37/08*** | (2006.01) |
| ***C07C 67/44*** | (2006.01) |

(52) U.S. Cl.
CPC ............. *B01J 23/892* (2013.01); *B01J 23/02* (2013.01); *B01J 35/394* (2024.01); *B01J 35/40* (2024.01); *B01J 35/52* (2024.01); *B01J 37/0072* (2013.01); *B01J 37/04* (2013.01); *B01J 37/088* (2013.01); *C07C 67/44* (2013.01); *B01J 2235/00* (2024.01); *B01J 2235/15* (2024.01); *B01J 2235/30* (2024.01)

(58) Field of Classification Search
CPC ........ B01J 23/892; B01J 35/394; B01J 35/50; B01J 23/02; B01J 37/0072; B01J 37/04; B01J 37/088; B01J 35/40; B01J 35/52; C07C 67/44
See application file for complete search history.

(56) References Cited

U.S. PATENT DOCUMENTS

| | | | |
|---|---|---|---|
| 3,436,358 | A | 4/1969 | Thygesen et al. |
| 3,901,827 | A | 8/1975 | Sinfelt et al. |
| 3,953,363 | A | 4/1976 | Yamauchi et al. |
| 4,035,263 | A | 7/1977 | Umemura et al. |
| 4,374,046 | A | 2/1983 | Antos |
| 4,518,796 | A | 5/1985 | Aoshima et al. |
| 4,536,482 | A | 8/1985 | Carcia |
| 4,562,174 | A | 12/1985 | Stiles |
| 4,698,324 | A | 10/1987 | Haruta et al. |
| 4,711,870 | A | 12/1987 | Yamada et al. |
| 4,959,338 | A | 9/1990 | Miura et al. |
| 4,992,408 | A | 2/1991 | Jackson |
| 5,002,922 | A | 3/1991 | Irgang et al. |
| 5,094,996 | A | 3/1992 | Kidd |
| 5,128,114 | A | 7/1992 | Schwartz |
| 5,254,705 | A | 10/1993 | Hattori et al. |
| 5,472,928 | A | 12/1995 | Scheuerman et al. |
| 5,494,879 | A | 2/1996 | Jin et al. |
| 5,506,273 | A | 4/1996 | Haruta et al. |
| 5,883,036 | A | 3/1999 | Fujie et al. |
| 6,057,442 | A | 5/2000 | Wulff-Döring et al. |
| 6,103,894 | A | 8/2000 | Degelmann et al. |
| 6,228,800 | B1 | 5/2001 | Yamaguchi et al. |
| 6,347,046 | B1 | 2/2002 | Ono et al. |
| 6,432,868 | B1 | 8/2002 | Marchal-George et al. |
| 6,514,905 | B1 | 2/2003 | Hanaki et al. |
| 6,635,191 | B2 | 10/2003 | Figueroa et al. |
| 6,660,897 | B1 | 12/2003 | Marchal-George et al. |

(Continued)

FOREIGN PATENT DOCUMENTS

| | | |
|---|---|---|
| CN | 1123527 A | 5/1996 |
| CN | 1512915 A | 7/2004 |

(Continued)

OTHER PUBLICATIONS

ACS Catal. 2013, 3, 1845-1849 (Suzuki et al., IDS reference with Supporting Information) (Year: 2013).*
JP2019001775A (Nagata et al. English language machine translation) (Year: 2019).*
WO 2018030384 A1 (Nagata-2, English language machine translation) (Year: 2018).*
Anandharamakishnan et al., "Spray Drying Techniques for Food Ingredient Encapsulation," John Wiley & Sons, Ltd., First Edition, 2015, pp. 1-36.
Eckhard et al., "Variation der Produkteigenschaften sprühgetrockneter Nanoskaliger SiQ2-Granulate," Symposium Produktgestaltung in der Partikeltechnologie 2011, 2011, URL: <https://publicarest.fraunhofer.de/server/api/core/bitstreams/030023a4-5670-461b-9256-32a6b755ae7e/content>.

(Continued)

*Primary Examiner* — Amy C Bonaparte
*Assistant Examiner* — Derek Rhoades
(74) *Attorney, Agent, or Firm* — Birch, Stewart, Kolasch & Birch, LLP

(57) ABSTRACT

A catalyst for production of carboxylic acid ester, containing:

catalyst metal particles; and
a support supporting the catalyst metal particles,
wherein the catalyst has a hollow particle ratio of 40% or less.

15 Claims, No Drawings

(56) References Cited

U.S. PATENT DOCUMENTS 6,706,659 B2 3/2004 Gillespie et al.
6,723,678 B2 4/2004 Gorer
6,846,471 B2 1/2005 Hotta et al.
6,861,387 B2 3/2005 Ruth et al.
6,921,605 B2 7/2005 Gorer
6,930,073 B2 8/2005 Dou
7,005,059 B1 2/2006 Quartararo et al.
7,005,406 B2 2/2006 Suenaga et al.
7,105,107 B2 9/2006 Ramani et al.
7,109,145 B2 9/2006 Ruth et al.
7,119,045 B2 10/2006 Magna et al.
7,176,159 B1 2/2007 Wheelock et al.
7,268,097 B2 9/2007 Katsuno et al.
7,361,626 B2 4/2008 Baijense et al.
7,422,995 B2 9/2008 Baijense et al.
7,528,092 B2 5/2009 Berben et al.
7,662,740 B2 2/2010 Chondroudis et al.
7,811,965 B2 10/2010 Cendak et al.
8,450,235 B2 5/2013 Suzuki et al.
2001/0025008 A1 9/2001 Hu et al.
2002/0062039 A1 5/2002 Salem et al.
2003/0040635 A1 2/2003 Jansen et al.
2003/0060655 A1 3/2003 Hayashi et al.
2004/0238410 A1 12/2004 Inoue et al.
2005/0054792 A1 3/2005 Kilty et al.
2005/0131255 A1 6/2005 Benderly et al.
2006/0014980 A1 1/2006 Kawato et al.
2006/0084830 A1 4/2006 Ryu
2007/0021629 A1 1/2007 Stevenson et al.
2007/0179320 A1 8/2007 Hirota et al.
2007/0191651 A1 8/2007 Coupard et al.
2008/0177111 A1 7/2008 van Laar et al.
2008/0242537 A1 10/2008 Kubanek et al.
2008/0286176 A1 11/2008 Schirmeister et al.
2009/0221849 A1 9/2009 Begli et al.
2010/0029980 A1 2/2010 Johnston et al.
2010/0249448 A1 9/2010 Suzuki et al.
2011/0184206 A1 7/2011 Suzuki et al.
2013/0172599 A1 7/2013 Suzuki et al.
2018/0326400 A1 11/2018 Lygin et al.
2019/0084914 A1 3/2019 Krill et al.
2019/0262800 A1 8/2019 Nagata et al.
2019/0358613 A1 11/2019 Ernst et al.
2020/0061590 A1 2/2020 Tomoda et al.
2020/0165196 A1 5/2020 Nagata et al.

FOREIGN PATENT DOCUMENTS

CN 1915475 A 2/2007
CN 107519892 A 12/2017
CN 108126762 A 6/2018
CN 109046259 A 12/2018
CN 109562356 A 4/2019
CN 109821529 A 5/2019
CN 110248729 A 8/2019
CN 111072810 A 4/2020
DE 10 2005 041 532 A1 3/2007
DE 10 2007 004 558 A1 8/2007
EP 1 283 206 A2 2/2003
EP 1 459 803 A1 9/2004
EP 1 495 802 A1 1/2005
EP 1 518 600 A1 3/2005
EP 1 358 935 B1 9/2007
EP 2 177 267 A1 4/2010
EP 2 210 664 A1 7/2010
EP 2 617 679 A1 7/2013
EP 3 626 338 A1 3/2020
FR 2 882 531 A1 9/2006
GB 1 415 636 A1 11/1975
JP 45-34368 B 11/1970
JP 55-153743 U 11/1980
JP 60-96522 A 5/1985
JP 62-7902 B2 2/1987
JP 62-27041 A 2/1987
JP 6-256011 A 9/1994
JP 7-47273 A 2/1995
JP 7-313880 A 12/1995
JP 8-57323 A 3/1996
JP 8-215544 A 8/1996
JP 9-52044 A 2/1997
JP 9-286662 A 11/1997
JP 11-1490 A 1/1999
JP 2000-95514 A 4/2000
JP 2000-154164 A 6/2000
JP 2000-176285 A 6/2000
JP 2001-79402 A 3/2001
JP 2001-172222 A 6/2001
JP 2001-220367 A 8/2001
JP 2002-282876 A 10/2002
JP 2002-361086 A 12/2002
JP 2003-53188 A 2/2003
JP 2003-103174 A 4/2003
JP 2003-192632 A 7/2003
JP 2003-521364 A 7/2003
JP 2003-305366 A 10/2003
JP 2004-141828 A 5/2004
JP 2004-209406 A 7/2004
JP 2004-209408 A 7/2004
JP 2004-351364 A 12/2004
JP 2006-212571 A 8/2006
JP 2006-240920 A 9/2006
JP 2006-265361 A 10/2006
JP 2007-197396 A 8/2007
JP 2007-245068 A 9/2007
JP 2008-538323 A 10/2008
JP 2009-502491 A 1/2009
JP 4420991 B2 2/2010
JP 2010-221081 A 10/2010
JP 2010-221082 A 10/2010
JP 2010-221083 A 10/2010
JP 2010-222151 A 10/2010
JP 4674921 B2 4/2011
JP 4803767 B2 10/2011
JP 2011-529493 A 12/2011
JP 5335505 B2 11/2013
JP 5336234 B2 11/2013
JP 5336235 B2 11/2013
JP 2016-686 A 1/2016
JP WO 2018030384 A1 * 2/2018 .............. B01J 23/30
JP 2018-535825 A 12/2018
JP 2019001775 A * 1/2019 ........... C07C 253/24
JP 2020-1001 A 1/2020
KR 10-2010-0019569 A 2/2010
TW 200613053 A 5/2006
TW 200914130 A 4/2009
WO WO 00/43121 A1 7/2000
WO WO 2004/011138 A1 2/2004
WO WO 2005/037768 A1 4/2005
WO WO 2006/064685 A1 6/2006
WO WO 2006/079850 A1 8/2006
WO WO 2007/015620 A1 2/2007
WO WO 2009/022544 A1 2/2009
WO WO 2009/054462 A1 4/2009
WO WO 2012/035637 A1 3/2012
WO WO 2017/084969 A1 5/2017
WO WO 2018/235798 A1 12/2018

OTHER PUBLICATIONS

Suzuki et al., "Aerobic Oxidative Esterification of Aldehydes with Alcohols by Gold-Nickel Oxide Nanoparticle Catalysts with a Core-Shell Structure," ACS Catalysis, vol. 3, 2013, pp. 1845-1849.
Third Party Obvervation for European Application No. 21760142.6, dated Jul. 5, 2024.
International Search Report, issued in PCT/JP2021/007189, dated Apr. 27, 2021.
Written Opinion of the International Searching Authority, issued in PCT/JP2021/007189, dated Apr. 27, 2021.
Eckhard et al., "Variation of Product Properties of Granules Spray-Dried From Nanoscale SiO2", Chemie Ingenieur Technik, vol. 84, No. 3, 2012, pp. 335-342, with an English abstract.
European Search Report for European Application No. 21760142.6, dated Jul. 13, 2023.

(56) References Cited

OTHER PUBLICATIONS

International Preliminary Report on Patentability and English translation of the Written Opinion of the International Searching Authority for International Application No. PCT/JP2021/007189, dated Sep. 9, 2022.
Barrio et al., "Evaluation of Silica-Alumina-Supported Nickel Catalysts in Dibenzothiophene Hydrodesulphurisation," Applied Catalysis A: General, vol. 248, 2003, pp. 211-225.
Castano et al., "Enhancement of pyrolysis gasoline hydrogenation over Pd-promoted Ni/SIO2—Al2O3 catalysts," Fuel, vol. 86, 2007, pp. 2262-2274.
Chinese Office Action for Chinese Application No. 200880102565.3 dated Mar. 1, 2012.
Chinese Office Action for Chinese Application No. 200880112821.7 dated Feb. 22, 2012.
Chinese Office Action for Chinese Application No. 200880112821.7, dated Nov. 27, 2012.
Choudary et al., "The First Example of Activation of Molecular Oxygen by Nickel in Ni—Al Hydrotalcite: A Novel Protocol for the Selective Oxidation of Alcohols," Angewandte Chemie Int. Ed., vol. 40, No. 4, 2001, pp. 763-766.
Dai et al., "Photodegradation Catalyst Screening by Combinatorial Methodology," Applied Catalysis A: General, vol. 290, 2005, pp. 25-35.
English translation of International Preliminary Report on Patentability and Written Opinion of the International Searching Authority for International Application No. PCT/JP2010/066084, dated Apr. 9, 2013.
English translation of the International Search Report for International Application No. PCT/JP2008/069249, dated Mar. 3, 2009.
English translation of the International Search Report for International Application No. PCT/JP2010/066084, dated Dec. 21, 2010.
European Office Action for European Application No. 20952475.0, dated Aug. 29, 2023.
European Search Report for European Application No. 08791982.5-1270, dated Nov. 7, 2011.
European Search Report for European Application No. 08841939.5-1270, dated Nov. 17, 2011.
European Search Report for European Application No. 10857271.0, dated Feb. 2, 2015.
Ferreira et al., "Theoretical optical properties of composite metal-NiO films," Journal of Physics D: Applied Physics, vol. 36, 2003, pp. 2386-2392.
Fuson et al., "Double Bond Migration in 1,2-Diaroyl-1-cycloalkenes," The Journal of Organic Chemistry, vol. 27, No. 5, May 1962, pp. 1957-1961.
Grisel et al., "A Comparative Study of the Oxidation of CO and CH4 Over Au/MOx/Al2O3 Catalysts," Catalysis Today, vol. 64, 2001, pp. 69-81.
Han et al., "Modified extra-large mesoporous silica supported Au—Ni as a highly efficient catalyst for oxidative coupling of aldehydes with methanol," RSC Advances, vol. 4, 2014, pp. 58769-58772.
International Preliminary Report on Patentability and English translation of the Written Opinion of the International Searching Authority for International Application No. PCT/JP2008/063767, dated Mar. 9, 2010.
International Preliminary Report on Patentability and English translation of the Written Opinion of the International Searching Authority for International Application No. PCT/JP2008/069249, dated Jun. 1, 2010.
International Preliminary Report on Patentability and Written Opinion of the International Searching Authority for International Application No. PCT/JP2020/033660, dated Mar. 16, 2023, with an English translation.
International Preliminary Report on Patentability and Written Opinion of the International Searching Authority for International Application No. PCT/JP2021/013068, dated Oct. 5, 2023, with an English translation.
International Search Report for International Application No. PCT/JP2020/033660, dated Nov. 17, 2020, with an English translation.
International Search Report for International Application No. PCT/JP2021/013068, dated May 25, 2021, with an English translation.
Japanese Office Action for Japanese Patent Application No. 2009-068421, dated Jul. 30, 2013.
Japanese Office Action for Japanese Patent Application No. 2009-257201, dated Dec. 6, 2013.
Ji et al., "Simple Fabrication of Nano-Sized NiO2 Powder and Its Application to Oxidation Reactions," Applied Catalysis A: General, vol. 282, 2005, pp. 25-30.
Kawabata et al., "Nickel Containing Mg—Al hydrotalcite-type anionic clay catalyst for the oxidation of alcohols with molecular oxygen," Journal of Molecular Catalysis A: Chemical, vol. 236, 2005, pp. 206-215.
Korean Office Action for Korean Patent Application No. 10-2013-7003812, dated Apr. 22, 2014.
Nakagawa et al., "Oxidation with Nickel Peroxide. I. Oxidation of Alcohols," The Journal of Organic Chemistry, vol. 27, No. 5, May 1962, pp. 1597-1601.
Okuda et al., "Preparation of Ag—NiO Composite Powders by Spray Pyrolysis from AG and NI Loading Versatic Acid 10," Resources and Materials, vol. 118, 2002, pp. 91-94 (22 pages total).
Supplementary European Search Report for European Application No. 21933136.0, dated Apr. 19, 2024.
Taiwanese Office Action and Search Report for Taiwanese Application No. 097130712, dated Jul. 30, 2012.
Taiwanese Office Action and Search Report for Taiwanese Application No. 097140722, dated Sep. 27, 2012.

* cited by examiner

CATALYST FOR PRODUCTION OF CARBOXYLIC ACID ESTER, METHOD FOR PRODUCING CATALYST FOR PRODUCTION OF CARBOXYLIC ACID ESTER, AND METHOD FOR PRODUCING CARBOXYLIC ACID ESTER

TECHNICAL FIELD

The present invention relates to a catalyst for production of carboxylic acid ester, a method for producing a catalyst for production of carboxylic acid ester, and a method for producing carboxylic acid ester

BACKGROUND ART

As a method for producing industrially useful carboxylic acid esters, in the case of methyl methacrylate, for example, there has been industrially used a method in which methacrylic acid is produced by oxidizing methacrolein with oxygen followed by allowing the methacrylic acid to react with methanol to produce methyl methacrylate.

For example, in Patent Literature 1, as a method for producing carboxylic acid ester, there is suggested use of a catalyst for production of carboxylic acid ester, the catalyst including oxidized nickel and X (wherein X represents at least one element selected from the group consisting of nickel, palladium, platinum, ruthenium, gold, silver, and copper) supported by a support within a range of an atomic ratio of Ni/(Ni+X) of from 0.20 to 0.99. The catalyst for production of carboxylic acid ester includes a metal element that is inexpensive and has excellent reactivity, for the main catalyst component, instead of the conventional expensive noble metals. The catalyst is said to be capable of maintaining high reactivity.

CITATION LIST

Patent Literature

Patent Literature 1 Japanese Patent No. 4674921

SUMMARY OF INVENTION

Technical Problem

In production of carboxylic acid ester, improving mechanical strength of catalyst particles is important for maintaining reactivity. The mechanical strength of catalyst particles herein correlates with factors such as the amount of the support, the shape of the particles, and presence of voids in the particles.

As a result of intensive studies by the present inventors, among catalyst particles prepared by the method described in Patent Literature 1, particles having an abnormality on the surface thereof such as an opening or wrinkles have been scarcely observed. However, on observing the cross section of the particles, hollow particles having minute voids have been found to be included at a level of more than 40%. Moreover, among the factors described above, voids in such particles have been found to markedly affect reaction results.

As described above, the techniques described in Patent Literature 1 are considered to leave room for improvement, from the viewpoint of improvement in activity and selectivity for a catalyst to be used for production of carboxylic acid ester.

The present invention has been accomplished in light of the above problems involved in the conventional art, and it is an object thereof to provide a catalyst for production of carboxylic acid ester, the catalyst exhibiting high activity and high selectivity.

Solution to Problem

The present inventors have made extensive investigations to have consequently found that sufficient reduction in voids in catalyst particles enables a catalyst that exhibits high activity and high selectivity to be obtained.

That is, the present invention encompasses aspects as follows.

[1]

A catalyst for production of carboxylic acid ester, comprising:

catalyst metal particles; and a support supporting the catalyst metal particles, wherein the catalyst has a hollow particle ratio of 40% or less.

[2]

The catalyst for production of carboxylic acid ester according to [1], wherein the hollow particle ratio is 35% or less.

[3]

The catalyst for production of carboxylic acid ester according to [1] or [2], wherein a content of the support is from 80.0 to 99.9% by mass with respect to the catalyst for production of carboxylic acid ester.

[4]

The catalyst for production of carboxylic acid ester according to any of [1] to [3], wherein the catalyst metal particles comprise at least one element selected from the group consisting of nickel, cobalt, palladium, platinum, ruthenium, lead and gold, silver, and copper.

[5]

The catalyst for production of carboxylic acid ester according to any of [1] to [4], wherein the catalyst metal particles are composite particles comprising:

oxidized nickel and/or cobalt, and

X, wherein X represents at least one element selected from the group consisting of nickel, palladium, platinum, ruthenium, gold, silver, and copper.

[6]

The catalyst for production of carboxylic acid ester according to [5], wherein a compositional ratio between nickel or cobalt and X in the composite particles, in terms of a Ni/(Ni+X) atomic ratio or a Co/(Co+X) atomic ratio, is from 0.20 to 0.99.

[7]

The catalyst for production of carboxylic acid ester according to [5] or [6], wherein the composite particles comprise oxidized nickel and gold.

[8]

The catalyst for production of carboxylic acid ester according to any of [1] to [7], wherein the support comprises silica and alumina.

[9]

The catalyst for production of carboxylic acid ester according to any of [1] to [8], wherein the support further comprises an oxide of at least one basic metal component selected from the group consisting of an alkaline metal, an alkaline earth metal, and a rare earth metal.

[10]

The catalyst for production of carboxylic acid ester according to any of [1] to [9], wherein the support comprises silica, alumina, and magnesia.

[11]

A method for producing the catalyst for production of carboxylic acid ester according to any of [1] to [10], the method comprising:

- a step (A) of preparing a support precursor slurry comprising raw material for the support at a stirring rotational speed of 120 rpm or more and 600 rpm or less, the slurry being at a temperature of 5° C. or more and 60° C. or less and having a viscosity of 10 cp or more and 550 cp or less,
- a step (B) of supplying the support precursor slurry to a spray dryer to spray-dry the support precursor slurry at an inlet temperature of the spray dryer of 150° C. or more and 215° C. or less,
- a step (C) of calcining after the step (B) to obtain a support, and
- a step (D) of allowing the support to support the catalyst metal particles.

[12]

The method for producing a catalyst for production of carboxylic acid ester according to [11], wherein a spray drying apparatus having an inner diameter of 1000 mm or more is employed in the step (B).

[13]

A method for producing carboxylic acid ester comprising a step of reacting (a) an aldehyde and an alcohol or (b) one or two or more alcohols in a presence of the catalyst for production of carboxylic acid ester according to any of [1] to [10] and oxygen.

[14]

The method for producing carboxylic acid ester according to [13], wherein the aldehyde is acrolein and/or methacrolein.

[15]

The method for producing carboxylic acid ester according to [13] or [14], wherein the aldehyde is acrolein and/or methacrolein, and the alcohol is methanol.

Advantageous Effect of Invention

According to the present invention, a catalyst for production of carboxylic acid ester that exhibits high activity and high selectivity can be provided.

DESCRIPTION OF EMBODIMENT

Hereinbelow, an embodiment of the present invention (hereinbelow, referred to as "the present embodiment") will be described in detail. The present invention is not limited to the following present embodiment, and can be variously modified and implemented without departing from the gist.

[Catalyst for Production of Carboxylic Acid Ester]

A catalyst for production of carboxylic acid ester of the present embodiment is a catalyst for production of carboxylic acid ester comprising catalyst metal particles and a support supporting the catalyst metal particles, and having a hollow particle ratio of 40% or less. Being thus configured, the catalyst for production of carboxylic acid ester of the present embodiment exhibits high activity and high selectivity.

In the present embodiment, a hollow particle refers to a particle having an area occupied by voids of 1% or more with respect to the cross-sectional area, when the cross section of the catalyst for production of carboxylic acid ester is observed. A solid particle refers to a particle having an area occupied by voids of less than 1% or having no void.

A hollow particle ratio refers to a value obtained by observing a cross section of each catalyst particle in the catalyst for production of carboxylic acid ester with a scanning electron microscope, dividing the number of hollow particles by the total number of the particles observed, and multiplying the resultant by 100. An example of the scanning electron microscope to be employed is an ultra-high resolution analytical scanning electron microscope ("SU-70" manufactured by Hitachi High-Technologies Corporation). A method for measuring the hollow particle ratio will be described in examples described below. The cross section of catalyst particles may be formed by polishing a cured product of an embedding resin including the catalyst particles embedded therein or may be formed from the cured product using BIB (broad ion beam) or the like.

The "catalyst particles" herein are particles including catalyst metal particles and a support supporting the catalyst metal particles.

In the present embodiment, from the viewpoint of developing higher activity and higher selectivity, the hollow particle ratio is preferably 35% or less, more preferably 30% or less, and even more preferably 25% or less.

The lower limit of the hollow particle ratio is not particularly limited, and is preferably more than 0%, more preferably 1% or more, and even more preferably 2% or more, from the viewpoint of productivity of the catalyst.

The hollow particle ratio can be adjusted to, but is not limited to, 40% or less by adopting preferable production conditions for a catalyst for production of carboxylic acid ester described below, for example.

The catalyst for production of carboxylic acid ester of the present embodiment, having characteristics described above, can achieve high activity and higher selectivity and provides high activity and higher selectivity in synthesis of methyl methacrylate.

In the present embodiment, catalyst metal particles are not particularly limited as long as having a function of catalyzing a reaction for producing carboxylic acid ester. From the viewpoint of catalytic performance, the catalyst metal particles preferably include at least one element selected from the group consisting of nickel, cobalt, palladium, platinum, ruthenium, lead and gold, silver, and copper. From the viewpoint of further catalytic performance, the catalyst metal particles are more preferably composite particles including oxidized nickel and/or cobalt and X (wherein X represents at least one element selected from the group consisting of nickel, palladium, platinum, ruthenium, gold, silver, and copper), and the composite particles even more preferably include oxidized nickel or cobalt and gold.

In the present embodiment, the catalyst for production of carboxylic acid ester preferably has a supported layer in which the composite particles are localized. The term "supported layer in which the composite particles are localized" refers to a region in the support where composite particles are concentratedly supported. In the catalyst for production of carboxylic acid ester of the present embodiment, composite particles are preferably supported not randomly in the support but selectively in a certain region. This region is referred to as the "supported layer in which the composite particles are localized". In the catalyst for production of carboxylic acid ester, if the composite particles are concentrated in a certain region as compared with other portions, the region is the "supported layer in which the composite particles are localized". Thus, which region is a "supported layer in which the composite particles are localized" can be determined by X-ray microprobe analysis described below or from secondary electron reflected images obtained with a high-resolution scanning electron microscope. The supported layer in which the composite particles are localized is preferably present in a region extending from the surface of the catalyst for production of carboxylic acid ester to 40% of the equivalent diameter of the catalyst for production of carboxylic acid ester. When the supported layer in which the composite particles are localized is present in this region, the influence of the diffusion rate of the reaction material within the support is reduced, and the reaction activity tends to be improved.

The catalyst for production of carboxylic acid ester of the present embodiment can have various sizes including a substantial thickness or particle diameter on the order of μm to cm, and various shapes. Specific examples of the shape of the catalyst for production of carboxylic acid ester include, but are not limited to, various shapes such as spheres, ovals, cylinders, tablets, hollow cylinders, plates, rods, sheets, and honeycombs. The shape can be suitably changed according to the reaction form, and in a fixed bed reaction, for example, hollow cylindrical or honeycomb-shaped particles are selected due to their low pressure loss, while spherical particles are typically selected under conditions of suspension of a liquid phase slurry.

The term "equivalent diameter" referred to herein represents the diameter of spherical particles, or in the case of irregularly shaped particles, the diameter of a sphere having an equal volume as the particles or having a surface area equal to the surface area of the particles. For a method for measuring the equivalent diameter, the average particle diameter (volume-based) is measured using a laser diffraction/scattering particle size distribution measuring apparatus, and the resulting value is taken as the equivalent diameter. Alternatively, the number average particle diameter as measured with a scanning electron microscope (SEM) can also be used to represent the equivalent diameter.

The optimum range of the thickness of the supported layer in which the composite particles are localized is selected according to the thickness of the support, particle diameter, type of reaction, and reaction form. Since the "equivalent diameter of the catalyst for production of carboxylic acid ester" is usually the same as the "equivalent diameter of the support", the "equivalent diameter of the catalyst for production of carboxylic acid ester" can be determined from the equivalent diameter of the support.

For example, in the case of using a support having a large equivalent diameter of the catalyst for production of carboxylic acid ester of more than 200 μm (e.g., several mm or more), the catalyst is generally used in a liquid phase reaction having a comparatively slow reaction rate or in a vapor phase reaction. Thus, by providing a layer which supports the composite particles as an active component in the region extending from the surface of the catalyst for production of carboxylic acid ester to 40% of the equivalent diameter of the catalyst for production of carboxylic acid ester and in the region extending from the outer surface of the catalyst for production of carboxylic acid ester to 80 μm and supports no composite particles inside the catalyst for production of carboxylic acid ester, a catalyst for production of carboxylic acid ester less susceptible to the influence of the diffusion rate of the reaction material tends to be obtained. As a result, the composite particles can be effectively used.

On the other hand, when the equivalent diameter of the catalyst for production of carboxylic acid ester is 200 μm or less, the composite particles are preferably supported in the region extending from the surface of the catalyst for production of carboxylic acid ester to 30% of the equivalent diameter of the catalyst for production of carboxylic acid ester. In the case of using in a liquid phase reaction, in particular, the support has been designed to have a small particle diameter in line with the reaction because the influence of the reaction rate and the intrapore diffusion rates of reaction materials within the support occurs. In the present embodiment, reducing the thickness of the supported layer in which the composite particles are localized tends to enable a highly active catalyst for production of carboxylic acid ester to be obtained without reducing the particle diameter of the support. In this case, separation of the catalyst by settling is facilitated, and additionally, the catalyst can be advantageously separated using a small-volume separator. Meanwhile, if the volume of the portion in which composite particles in the catalyst for production of carboxylic acid ester are not supported becomes excessively large, the volume not required by the reaction per reactor increases, thereby resulting in waste in some cases. Accordingly, it is preferable to set the particle diameter of the support according to the reaction form and to set the required thickness of the supported layer in which the composite particles are localized and the thickness of the layer in which composite particles are not supported.

The catalyst for production of carboxylic acid ester may also have an outer layer substantially free of composite particles on the outside of the supported layer in which the composite particles are localized. The outer layer is preferably formed at a thickness of from 0.01 to 15 μm from the outer surface of the support. Providing the outer layer within this range enables the catalyst to be used as a catalyst that is strongly resistant to catalyst poisoning and from which falling-off of composite particles due to abrasion is suppressed, in reactions using a reactor such as a fluidized bed, bubble column, stirring reactor, or any other reactor for which friction of catalyst particles is of concern, and in reactions in which there occurs accumulation of poisoning substances. In addition, the outer layer can be controlled to be extremely thin, and thus large decrease in activity can be suppressed.

The optimum range of the thickness of the outer layer substantially free of composite particles is selected according to the reaction characteristics, physical properties of the support, amount of composite particles supported, and the like, and is preferably from 0.01 to 15 μm, more preferably from 0.1 to 10 μm, and even more preferably from 0.2 to 5 μm. When the thickness of the outer layer (composite particle-non-supported layer) is 15 μm or less, the catalyst activity can be more enhanced in use of the composite particles as a catalyst. When the thickness of the outer layer is 0.01 μm or more, falling-off of composite particles due to abrasion is suppressed, and the activity can be maintained for a longer period.

In the present embodiment, the term "substantially free of composite particles" means the substantial absence of a peak indicating the distribution of oxidized nickel and/or cobalt and X (wherein X represents at least one of elements selected from the group consisting of nickel, palladium, platinum, ruthenium, gold, silver, and copper) having a relative intensity of 10% or more in X-ray microprobe analysis described below or in secondary electron reflected images obtained with a high-resolution scanning electron microscope.

Preferable examples of the oxidized nickel that may comprise the composite particles of the present embodiment include nickel oxides formed by bonding nickel and oxygen (e.g., $Ni_2O$, NiO, $NiO_2$, $Ni_3O_4$, or $Ni_2O_3$), or composite oxides containing nickel such as nickel oxide compounds formed by bonding nickel and X and/or one or more other metal elements and oxygen, or a solid solution or mixture thereof.

Preferable examples of the oxidized cobalt that may comprise the composite particles of the present embodiment include cobalt oxides formed by bonding cobalt and oxygen (e.g., CoO, $Co_2O_3$, or $Co_3O_4$), or composite oxides containing cobalt such as cobalt oxide compounds formed by bonding cobalt and X and/or one or more other metal elements and oxygen, or a solid solution or mixture thereof.

The term "nickel oxide" referred to herein represents a compound containing nickel and oxygen. Nickel oxides include the previously exemplified $Ni_2O$, NiO, $NiO_2$, $Ni_3O_4$, $Ni_2O_3$, or hydrates thereof, hydroperoxides of nickel containing an OOH group, peroxides of nickel containing an $O_2$ group, and mixtures thereof.

The term "composite oxide" referred to herein represents an oxide containing two or more metals. The "composite oxide" refers to an oxide in which two or more metal oxides form a compound. Although including multiple oxides not containing an ion of an oxoacid as a structural unit (e.g., pervoskite oxides and spinel oxides of nickel), the composite oxide has a broader concept than that of multiple oxides, including all oxides in which two or more metals are compounded. Oxides in which two or more metal oxides form a solid solution are also within the scope of composite oxides.

In the catalyst for production of carboxylic acid ester of the present embodiment, on compounding nickel oxide and/or cobalt oxide with X as described above, the inherent catalytic ability of nickel oxide and/or cobalt oxide having oxidative esterification activity can be brought out, and a markedly high level of catalyst performance, which cannot be achieved with a catalyst composed of each component singly, tends to appear. This is thought to be because a unique effect developed by compounding nickel oxide and/or cobalt oxide and X, that is, a novel catalyst action completely different from that of each component singly, is generated by a dual functional effect between both the metal components, the formation of a new active species, or the like. Further, in the case of supporting oxidized nickel and/or oxidized cobalt and X on a support in a highly dispersed state, revolutionary catalyst performance unable to be obtained with conventional catalysts tends to be achieved.

For example, if gold is selected for X and nickel oxide and gold are supported on a support in a highly dispersed state, markedly high catalyst performance tends to appear. Such a catalyst for production of carboxylic acid ester has higher selectivity for carboxylic acid ester, in comparison with a catalyst in which each of nickel oxide or gold is supported singly on the support, and tends to exhibit improved activity at a specific compositional ratio of Ni/Au. The catalyst also exhibits high catalytic activity per metal atom as compared with a particle supported material composed of each component singly, and development of catalyst performance caused by the compounding is strongly dependent on the composition of nickel and gold supported. This is presumed to be due to the presence of an optimum ratio for formation of a nickel oxidation state that is optimum for the reaction. Since the two components: the nickel oxide and gold are dispersed and supported on a support in this manner, highly outstanding compounding effects, which cannot be predicted from the simple combined addition of each component singly, tends to be developed.

The catalyst for production of carboxylic acid ester in which gold is selected for X has the oxidized nickel and gold supported on a support in a highly dispersed state, and both the components tend to be compounded at the nano-size level. When such a catalyst for production of carboxylic acid ester is observed with a transmission electron microscope/scanning transmission electron microscope (TEM/STEM), typically a structure is observed in which nearly spherical nanoparticles of 2 to 3 nm are uniformly dispersed and supported on a support.

When the catalyst is subjected to an elementary analysis of the nanoparticles by energy dispersive X-ray spectrometry (EDS), typically, the catalyst is observed to be in a form in which nickel and gold coexist in all the particles and the surface of gold nanoparticles is coated with nickel, and also a nickel component is observed to be singly supported on the support in addition to the nanoparticles containing nickel and gold.

Further, subjecting the catalyst to X-ray photoelectron spectroscopy (XPS) and powder X-ray diffraction (powder XRD) enables the state of existence of the metals to be confirmed. Typically, while gold is observed to exist as a crystalline metal, nickel is observed to exist as an amorphous oxide having a valence of 2.

Further, when the catalyst is subjected to ultraviolet-visible spectroscopy (UV-Vis), with which change in the excited state of electrons can be observed, typically, a surface plasmon absorption peak (at about 530 nm) originating from gold nanoparticles observed in gold nanoparticles of a single metal species is observed to disappear due to compounding of nickel oxide and gold. The phenomenon of disappearance of this surface plasmon absorption peak has not been observed in catalysts composed of combinations of gold and metal oxide species other than nickel oxide not observed to have any effect on the reaction (e.g., metal oxides such as chromium oxide, manganese oxide, iron oxide, cobalt oxide, copper oxide, and zinc oxide). The disappearance of this surface plasmon absorption peak is thought to be caused by the result of the formation of a mixed electron state via the contact interface between oxidized nickel and gold, that is, hybridization of two metallic chemical species.

Conversion to highly oxidized nickel oxide can be confirmed via color change of the catalyst and ultraviolet-visible spectroscopy (UV-Vis). As a result of adding gold to nickel oxide, the nickel oxide changes in color from grayish green to brown, and the UV spectrum demonstrates absorbance over nearly the entire visible light region. The shape of the UV spectrum and the color of the catalyst are similar to those of a highly oxidized nickel oxide ($NiO_2$) measured as a reference sample. As described above, the nickel oxide is presumed to be converted to a highly oxidized nickel oxide due to the addition of gold.

From the above results, the structure of the composite particles in the case of selecting gold for X is believed to be in a form in which the gold particles serve as the core and the surface thereof is coated with a highly oxidized nickel oxide, without any gold atoms present on the surface of the composite particles.

The compositional ratio between nickel or cobalt and X in the composite particles, in terms of a Ni/(Ni+X) atomic ratio or a Co/(Co+X) atomic ratio, is preferably from 0.20 to 0.99, more preferably from 0.30 to 0.90, and even more preferably from 0.50 to 0.90. The term "Ni/(Ni+X) atomic ratio" herein refers to a ratio of the number of atoms of nickel supported on the support to the total number of atoms of nickel and X, and the term "Co/(Co+X) atomic ratio" refers to a ratio of the number of atoms of cobalt supported on the support to the total number of atoms of cobalt and X.

The composite particles are preferably supported on the support in a highly dispersed state. The composite particles are more preferably dispersed and supported in the form of microparticles or a thin film, and the average particle diameter thereof is preferably from 2 to 10 nm, more preferably from 2 to 8 nm, and even more preferably from 2 to 6 nm.

When the average particle diameter of the composite particles is within the above ranges, a specific active species structure composed of nickel and/or cobalt and X is formed, and the reaction activity tends to improve. Here, the average particle diameter in the present embodiment means the number average particle diameter as measured with a transmission electron microscope (TEM). Specifically, in an image observed with a transmission electron microscope, an area of black contrast indicates composite particles. The diameter of each of all the particles is measured, and the number average thereof can be calculated therefrom.

The form of the composite particles is not particularly limited as long as both of the components of nickel and/or cobalt and X are contained therein. Preferable is a form that includes both the components preferably coexisting in the particles and has a phase structure, that is, any one of structures such as a solid solution structure in which chemical species randomly occupy crystal sites, a core-shell structure in which each chemical species is separated in the shape of concentric spheres, an anisotropic phase separation structure in which phases are separated anisotropically, or a heterobondphilic structure in which both chemical species are present adjacent to each other on the particle surface. More preferable is a form in which the particles have a core composed of X and the surface of the cores is coated with oxidized nickel and/or cobalt. The shape of the composite particles is not particularly limited as long as both the components are contained therein, and may take any shape such as spherical, hemispherical, or the like.

As described above, transmission electron microscopy/scanning transmission electron microscopy (TEM/STEM), for example, is effective as an analysis technique for observing the form of the composite particles. Elementary analyses within the particles and visualization of images of the distribution of elements therein are enabled by irradiating nanoparticles observed by TEM/STEM with an electron beam. The composite particles of the present embodiment contain nickel and/or cobalt and X in all of the particles as will be indicated in the examples to be described below, and have been confirmed to have a form in which the surface of X is coated with nickel and/or cobalt. In the case in which the particles have such a form, the atomic ratio of nickel and/or cobalt to X varies according to the locations of the composition analysis points in the particles, and nickel and/or cobalt is detected in larger amounts on the edges of the particles than in the central portion thereof. Thus, the atomic ratio of nickel or cobalt to X may vary depending on the locations of the analysis points even among individual particles, and the range thereof is included in the range of the Ni/(Ni+X) atomic ratio or the Co/(Co+X) atomic ratio as described above.

In the case in which gold, silver, or copper is selected for X, ultraviolet-visible spectroscopy (UV-Vis) is an effective means of identifying the structure thereof. In the case of nanoparticles of gold, silver, or copper singly, the photoelectric field in the visible to near infrared region is coupled with free electrons on the surface of the metal, indicating surface plasmon absorption. For example, when a catalyst including gold particles supported is irradiated with visible light, an absorption spectrum is observed that is based on plasmon resonance originating from gold particles at a wavelength of about 530 nm. However, in the catalyst for production of carboxylic acid ester including nickel oxide and gold supported according to the present embodiment, since the surface plasmon absorption thereof disappears, gold can be considered not to be present on the surface of the composite particles of the present embodiment.

The solid form of the nickel is not particularly limited as long as the predetermined activity is obtained, and preferred is an amorphous form having no diffraction peak observed in X-ray diffraction. With such a form, in use as a catalyst for an oxidation reaction, interaction with oxygen is presumed to increase. Additionally, the bonding interface between the oxidized nickel and X increases, and thus better activity tends to be obtained.

In the present embodiment, X is at least one element selected from the group consisting of nickel, palladium, platinum, ruthenium, gold, silver, and copper. X is more preferably selected from nickel, palladium, ruthenium, gold, and silver.

The chemical state of X may be a metal, an oxide, an hydroxide, a composite compound containing X and nickel, cobalt, or one or more another metal elements, or a mixture thereof, and a preferable chemical state is a metal or oxide and more preferably a metal. The solid form of X is not particularly limited as long as the predetermined activity can be obtained, and the form may be either a crystalline form or an amorphous form.

The term "another metal element" herein refers to a third component element or a metal component such as an alkaline metal, an alkaline earth metal, or a rare earth metal to be contained in the catalyst for production of carboxylic acid ester, besides a constituent element of the support to be described below, oxidized nickel and/or cobalt and X.

The catalyst for production of carboxylic acid ester of the present embodiment has oxidized nickel and/or cobalt and X supported on a support as described above, and exerts excellent effects as a result of forming composite particles composed of oxidized nickel and/or cobalt and X. The term "composite particle" herein refers to a particle containing different binary metal species in a single particle. Examples of binary metal species different from this include binary metal particles in which both nickel and/or cobalt and X are metals and metal particles forming an alloy or intermetallic compound of nickel and/or cobalt and X. In the case of using these as catalysts for chemical synthesis, the selectivity of the target product and the catalyst activity tend to be lower as compared with the catalyst for production of carboxylic acid ester of the present embodiment.

The catalyst for production of carboxylic acid ester of the present embodiment preferably contains oxidized nickel and/or cobalt singly on the support in addition to the composite particles composed of oxidized nickel and/or cobalt and X. The presence of oxidized nickel and/or cobalt not compounded with X further enhances the structural stability of the catalyst for production of carboxylic acid ester and inhibits increase in the pore diameter caused by a prolonged reaction as well as the accompanying growth of the composite particles. This effect becomes marked when the support contains silica and alumina, and becomes more marked when the support contains silica, alumina, and magnesia (i.e., contains an aluminum-containing silica-based composition containing silica, alumina, and magnesia), as will be described below.

Hereinafter, there will be described action that enhances the structural stability of the catalyst for production of carboxylic acid ester and that inhibits increase in the pore diameter caused by a prolonged reaction as well as the accompanying growth of composite particles by allowing oxidized nickel and/or cobalt singly to be present on the support.

As will be described below, in a synthesis reaction of carboxylic acid ester, by-production of acetal or the like caused by acidic substances exemplified by methacrylic acid or acrylic acid, which is a by-product unique to the production reaction of carboxylic acid ester, can be inhibited by adding a compound of an alkaline metal or alkaline earth metal to the reaction system to maintain the pH of the reaction system at 6 to 9, and more preferably at neutral conditions (e.g., pH 6.5 to 7.5), that is, as close to pH 7 as possible.

According to studies conducted by the present inventors, in the case of carrying out a prolonged reaction according to the reaction procedure using a gold particle supported material in which single-component gold particles are supported on a support composed of an aluminum-containing silica-based composition containing silica and alumina, structural changes tend to occur, although gradually, in the gold particle supported material. This phenomenon is thought to be caused by increase in the pore diameter of the supported material particles, which increase is brought about because the supported material particles are locally and repeatedly exposed to acid and base by the reaction procedure, and thus a portion of the Al in the support dissolves and precipitates, resulting in rearrangement of the silica-alumina crosslinked structure. In addition, accompanying the change of increase in the pore diameter, sintering of the gold particles occurs to cause the surface area to be decreased, and thus the catalyst activity tends to decrease.

On the other hand, the presence of composite particles and oxidized nickel and/or cobalt singly on the support enhances the structural stability of the supported material particles according to the reaction procedure described above, and increase in the pore diameter and growth of the composite particles tend to be inhibited. As described above, the formation of a nickel and/or cobalt oxide compound or a composite oxide containing nickel and/or cobalt in the form of a solid solution and the like due to reaction of oxidized nickel and/or cobalt with constituent elements of the support is considered to be a factor behind the reason. As a result of action of such a nickel compound on stabilization of the silica-alumina crosslinked structure, structural change in the supported material particles is thought to have greatly improved. The present inventors have presumed that the appearance of the structural stabilizing effect of this supported material is attributable to the oxidized nickel and/or cobalt present in the support. For this reason, this effect is naturally obtained when oxidized nickel and/or cobalt contained in composite particles is in contact with the support, and an even greater stabilizing effect is thought to be obtained when oxidized nickel and/or cobalt is present singly on the support.

The support of the catalyst for production of carboxylic acid ester of the present embodiment is not particularly limited as long as the support can support oxidized nickel and/or cobalt and X, and conventional catalyst supports used for chemical synthesis can be used.

Examples of supports include various types of supports such as activated carbon, silica, alumina, silica-alumina, titania, silica-titania, zirconia, magnesia, silica-magnesia, silica-alumina-magnesia, calcium carbonate, zinc oxide, zeolite, and crystalline metallosilicate. Preferable examples of supports include activated carbon, silica, alumina, silica-alumina, silica-magnesia, silica-alumina-magnesia, titania, silica-titania, and zirconia, and more preferable examples include silica-alumina and silica-alumina-magnesia.

At least one metal component selected from the group consisting of alkaline metals (Li, Na, K, Rb, and Cs), alkaline earth metals (Be, Mg, Ca, Sr, and Ba), and rare earth metals (La, Ce, and Pr) may be supported on the support. Metal components to be supported on the support are preferably metal components that become oxides by calcining or the like, such as nitrates or acetates.

A support composed of an aluminum-containing silica-based composition containing silica and aluminum is preferably used for the support. In other words, the support preferably contains silica and alumina. The support has higher water resistance than that of silica and higher acid resistance than that of alumina. The support comprises characteristics superior to those of conventional supports typically used, including greater hardness and higher mechanical strength than those of activated carbon, and is also able to stably support the active components: oxidized nickel and/or cobalt and X. Consequently, the catalyst for production of carboxylic acid ester can maintain high reactivity over a long period.

The catalyst for production of carboxylic acid ester having a specific atomic ratio for oxidized nickel and/or cobalt and X and including an aluminum-containing silica-based composition for the support, when used as a catalyst for chemical synthesis, has high mechanical strength, is physically stable, and satisfies corrosion resistance with respect to liquid properties unique to the reaction while having a large surface area suitable for use as a catalyst support.

Hereinafter, there will be described the characteristics of a support composed of an alumina-containing silica-based composition containing silica and alumina of the present embodiment, which has enabled the catalyst life to considerably improved. Reasons why the mechanical strength and chemical stability of the support have been able to be greatly improved are presumed as follows.

In the support composed of an aluminum-containing silica-based composition, addition of aluminum (Al) to a uncrosslinked silica (Si—O) chain of a silica gel leads to new formation of Si—O—Al—O—Si bonds, and it is considered that the formation of an Al-crosslinked structure without any loss of the inherent stability to acidic substances of the Si—O chain has allowed the Si—O bonds to be strengthened and the stability of hydrolysis resistance (hereinafter, simply referred to as "water resistance") to be considerably improved. When a Si—O—Al—O—Si crosslinked structure is formed, the number of uncrosslinked Si—O chains decreases in comparison with the case of silica gel singly, and also the mechanical strength is thought to increase. That is, the number of Si—O—Al—O—Si structures formed and improvement of the mechanical strength and water resistance of the resulting silica gel is presumed to be correlated.

One of the reasons why the oxidized nickel and/or cobalt and X can be stably supported on a support for a long period is that the support has greatly improved mechanical strength and chemical stability, as described above, and comprises superior physical properties in comparison with typically used conventional supports. As a result, it is considered that nickel and/or cobalt and X, the active components, are unlikely to be separated from the support and can be stably supported over a long period.

In a commonly used support such as silica or silica-titania, nickel and/or cobalt components are observed to elute from the support, although gradually, in prolonged reactions. In contrast, when the support described above is used, the present inventors have found that elution of nickel and/or cobalt components is suppressed over a long period. On the basis of the results of X-ray photoelectron spectroscopy (XPS), transmission electron microscopy (TEM/EDX), and a double crystal high-resolution X-ray fluorescence method (HRXRF), when a silica or silica-titania support is used, eluted nickel and/or cobalt components have been confirmed to be nickel oxide or cobalt oxide present singly on the support. Since nickel oxide or cobalt oxide is a compound soluble in acid, when used for a catalyst for carboxylic acid ester synthesis, the oxide is presumed to be eluted by an acidic substance typified by methacrylic acid or acrylic acid that are unique by-products of the reaction.

On the basis of analyses of the chemical state of nickel and/or cobalt by a double crystal high-resolution X-ray fluorescence method (HRXRF), as for the nickel and/or cobalt in the catalyst for production of carboxylic acid ester of the present embodiment, it is presumed that there has been formed not only nickel oxide and/or cobalt oxide as a single compound but also a composite oxide containing nickel and/or cobalt such an oxidized compound of nickel and/or cobalt formed as a result of bonding between nickel oxide and/or cobalt oxide and constituent component elements of the support, or a solid solution or mixture thereof.

The double crystal high-resolution X-ray fluorescence method (HRXRF) has extremely high energy resolution and is able to analyze a chemical state from the energy levels (chemical shifts) and shapes of the resulting spectrum. In the $K\alpha$ spectra of 3d transition metal elements in particular, changes appear in the chemical shift and shape due to changes in the valence or electronic state, thereby making it possible analyze the chemical state in detail. In the catalyst for production of carboxylic acid ester of the present embodiment, changes appear in the $NiK\alpha$ spectrum, and a chemical state was confirmed for nickel that differs from that of nickel oxide as a single compound.

For example, nickel aluminate, which is formed from nickel oxide and alumina, is a compound insoluble in acid. As a result of forming such a nickel compound on a support, elution of the nickel component is presumed to have been greatly improved.

In a preferable elementary composition of the support composed of an aluminum-containing silica-based composition containing silica and alumina, the amount of aluminum is in the range of from 1 to 30 mol %, preferably from 5 to 30 mol %, and more preferably from 5 to 25 mol % based on the total molar amount of silicon and aluminum. When the amount of aluminum is within the above ranges, acid resistance and mechanical strength tend to be satisfactory.

The support in the catalyst for production of carboxylic acid ester of the present embodiment preferably further contains an oxide of at least one basic metal selected from the group consisting of alkaline metals, alkaline earth metals, and rare earth metals, in addition to silica and alumina, from the viewpoint of further improving mechanical strength and chemical stability. Examples of alkaline metals of the basic metal components include Li, Na, K, Rb, and Cs, examples of alkaline earth metals include Be, Mg, Ca, Sr and Ba, and examples of rare earth metals include La, Ce, and Pr. Among those described above, Mg as an alkaline earth metal is preferable, and the support especially preferably contains silica, alumina, and magnesia.

In the elementary composition of the support containing silica, alumina, and an oxide of at least one basic metal selected from the group consisting of alkaline metals, alkaline earth metals, and rare earth metals, the amount of aluminum is in the range of from 1 to 30 mol %, preferably from 5 to 30 mol %, and more preferably from 5 to 25 mol % based on the total molar amount of silicon and aluminum. The compositional ratio between the basic metal oxide and alumina, in terms of the atomic ratio of (alkaline metal+1/2×alkaline earth metal+1/3×rare earth metal)/Al, is preferably in the range of from 0.5 to 10, more preferably from 0.5 to 5.0, and even more preferably from 0.5 to 2.0. When the elementary composition of silica, alumina, and basic metal oxide is within the above ranges, the silicon, aluminum, and the basic metal oxide form a specific stable bonding structure, and as a result, the mechanical strength and water resistance of the support tend to be satisfactory.

Next, a method for preparing a support having a composition as described above will be described.

The method for preparing a support composed of an aluminum-containing silica-based composition containing silica and alumina is not particularly limited. For example, the support can be prepared by calcining an aluminum-containing silica-based composition to be obtained according to methods of (1) to (5) below under conditions described below.

(1) A commercially available silica-alumina compound is used.

(2) A silica sol is allowed to react with an aluminum compound solution.

(3) A silica sol is allowed to react with an aluminum compound insoluble in water.

(4) A silica gel is allowed to react with an aqueous solution of a water-soluble aluminum compound.

(5) A silica gel and an aluminum compound are subject to a solid phase reaction.

Hereinafter, the support preparation methods of (2) to (5) above will be described in detail.

In the methods of (2) to (5) above, a silica sol or silica gel is used for the silica source. The silica gel is only required to have uncrosslinked Si sites that react with Al, and the length of the Si—O chain is not particularly restricted. The aluminum compound is preferably a water-soluble compound such as sodium aluminate, aluminum chloride hexahydrate, aluminum perchlorate hexahydrate, aluminum sulfate, aluminum nitrate nonahydrate, or aluminum diacetate, but a compound insoluble in water, such as aluminum hydroxide or aluminum oxide, can also be used as long as being a compound that reacts with uncrosslinked Si in the silica sol and silica gel.

In the case of the methods of (2) and (3), in which a silica sol is used as a starting material, after obtaining a mixed sol containing the silica sol and an aluminum compound by mixing the silica sol and the aluminum compound, the mixed sol is subjected to a multi-stage hydrothermal reaction at 10 to 100° C. for 1 to 48 hours and dried to obtain a gel followed by calcining under temperature, time and atmospheric conditions described below. Alternatively, an alkaline aqueous solution is added to the above mixed sol followed by co-precipitating the silica and an aluminum compound and drying and calcining under conditions described below. It is also possible to obtain a support composed of an aluminum-containing silica-based composition having a desired particle diameter by a step such as a step of micronizing the above mixed sol directly using a spray dryer, a step of drying the mixed sol followed by granulating the gel, or the like. On micronization using a spray dryer, as described below, the mixed sol (support precursor slurry) is preferably supplied to a spray dryer with its temperature adjusted to 5° C. or more and 60° C. or less and its viscosity adjusted to 10 cp or more and 550 cp or less.

Particularly, in the case of the method of (3), a silica sol is allowed to react with an aluminum compound insoluble in water, and at this time, the aluminum compound can be pulverized in advance to a predetermined particle diameter or can be preliminarily coarsely pulverized. The silica sol and the water-insoluble aluminum compound are mixed and allowed to react with each other. Then, the reaction product is dried and further calcined under conditions described below. The calcined silica-alumina compound may also be pulverized to a predetermined particle diameter without pre-pulverization of the aluminum compound.

In the method of (5), which uses a silica gel for the starting material as well, an aluminum-containing silica composition is prepared by subjecting the silica gel and an aluminum compound to a solid phase reaction. The Al is allowed to react in a solid phase state with uncrosslinked Si. The silica gel and the aluminum compound may be pulverized to a predetermined particle diameter in advance or may also be preliminarily coarsely pulverized. Pulverization may be carried out for each substance singly or after mixing both substances. Calcining is carried out under temperature, time and atmospheric conditions described below. Without preliminarily pulverization of the silica gel and aluminum compound, the resulting aluminum-containing silica composition can also be pulverized after the reaction to a predetermined particle diameter before use.

In a method for preparing a support containing silica, alumina, and an oxide of at least one of basic metals including alkaline metals, alkaline earth metals, and rare earth metals, in accordance with the above method for preparing a support composed of an aluminum-containing silica-based composition containing silica and alumina, the support can be prepared by drying a support precursor slurry obtained by mixing an alkaline metal oxide, alkaline earth metal oxide and/or rare earth metal oxide into silica and aluminum components, and further calcining the dried slurry under conditions described below.

A common commercially available compound can be used as a raw material of the alkaline metal, alkaline earth metal, or rare earth metal in the same manner as the aluminum raw material. The raw material is preferably a water-soluble compound and more preferably a hydroxide, carbonate, nitrate, or acetate.

Another preparation method that can be used is a method in which a basic metal component selected from the group consisting of alkaline metals, alkaline earth metals, and rare earth metals is adsorbed onto a support composed of an aluminum-containing silica-based composition. For example, there can be applied a method using an immersion method in which a support is added to a liquid including a basic metal compound dissolved followed by drying treatment or the like, or a method using an impregnation method in which a basic compound equivalent to the pore volume is allowed to permeate into a support followed by drying treatment. However, a method in which the basic metal component is adsorbed later requires caution such as conducting liquid drying treatment under mild conditions for allowing the basic metal component to be highly dispersed in the support.

An inorganic substance or organic substance can be added to the support precursor slurry that is a mixture of the various raw materials described above, in order to control slurry properties and finely adjust the pore structure or other characteristics of the product or the properties of the resulting support.

Specific examples of inorganic substances to be used include mineral acids such as nitric acid, hydrochloric acid, and sulfuric acid, salts of metals including alkaline metals such as Li, Na, K, Rb, and Cs and alkaline earth metals such as Mg, Ca, Sr, and Ba, water-soluble compounds such as ammonia or ammonium nitrate, and clay minerals that are dispersed in water to form a suspension. Specific examples of organic substances include polymers such as polyethylene glycol, methyl cellulose, polyvinyl alcohol, polyacrylic acid, and polyacrylamide.

There are various effects of addition of inorganic substances and organic substances, and the main effects include formation of a spherical support, controlling the pore diameter and pore volume, and the like. Specifically, the liquid properties of the support precursor slurry are an important factor in obtaining a spherical support. Adjusting the viscosity and solid content using an inorganic substance or inorganic substance enables the liquid properties to be altered so as to easily obtain a spherical support. It is also preferable to appropriately select and use an optimum organic compound that remains inside the support at the molding stage of the support and the residual substance of which can be removed by calcining and washing operations after the molding.

Next, a method in which spray-drying is conducted to preparing a support will be described, as a preferable method for preparing a support.

In the present embodiment, a support is prepared by a method including a step (A) of preparing a support precursor slurry comprising raw material for the support at a stirring rotational speed of 120 rpm or more and 600 rpm or less, the support precursor slurry being at a temperature of 5° C. or more and 60° C. or less and having a viscosity of 10 cp or more and 550 cp or less, a step (B) of supplying the support precursor slurry to a spray dryer to spray-dry the support precursor slurry at an inlet temperature of the spray dryer of 150° C. or more and 215° C. or less, and a step (C) of calcining the spray-dried precursor slurry after the step (B) to obtain a support.

In the step (A), while the temperature and viscosity of the support precursor slurry obtained as described above are maintained at 5° C. or more and 60° C. or less and 10 cp or more and 550 cp or less, respectively, the slurry is aged. When the temperature and viscosity of the support precursor slurry are adjusted within the ranges described above, a hollow particle ratio desired in the present embodiment tends to be achieved. The viscosity herein refers to a viscosity measured at the temperature of the support precursor slurry. During preparation of the support precursor slurry, the slurry is aged while the stirring rotational speed is maintained at 120 rpm or more and 600 rpm or less. When the stirring rotational speed is set within the range described above, generation of bubbles in the slurry tends to be suppressed. The shape of a stirring blade is not particularly limited, and example thereof include an anchor-type stirring blade, a paddle-type stirring blade, and a turbine-type stirring blade. From the viewpoint of shearing performance, a paddle-type stirring blade and a turbine-type stirring blade are preferable, and a turbine-type stirring blade is more preferable. Examples of the turbine-type stirring blade include a radial flow turbine blade, an axial flow turbine blade, and an edged turbine blade.

In the step (B), the support precursor slurry obtained in the step (A), which has a temperature of 5° C. or more and 60° C. or less and a viscosity of 10 cp or more and 550 cp or less, is supplied to a spray dryer, and the support precursor slurry is spray-dried with the inlet temperature of the spray dryer set at 150° C. or more and 215° C. or less.

When the inlet temperature of the spray dryer is adjusted within the range described above, a hollow particle ratio desired in the present embodiment tends to be achieved. In the case of an inlet temperature of the spray dryer higher than 215° C., even if the temperature and viscosity of the support precursor slurry are adjusted within the preferable ranges described above, a desired hollow particle ratio tends to be difficult to achieve. The shape of the spray dryer is not particularly limited, and the inner diameter of the spray dryer is indicated as the maximum diameter of the drying chamber. Generally, a precursor slurry is sprayed from the upper center of the drying chamber of the spray dryer, and the precursor slurry comes in contact with heated air supplied separately from the upper portion of the drying chamber to thereby carry out drying. The dried particles thus obtained are removed from the lower portion of the drying chamber of the spray dryer and subjected to the next step (calcining step). The inlet temperature of the spray dryer can be identified as the hot air temperature at the drying chamber inlet of the spray dryer and can be adjusted within the above range via the temperature of the hot air.

The reason why the hollow particle ratio can be lower under the conditions described above is not certain but is considered to be due to the following factor. Subjection to the step (A) enables a support precursor slurry to be obtained, with which hollows are unlikely to be formed. Then, in the spray-drying step, it is considered that the support precursor slurry turns into spherical droplets, the droplets are scattered in air, moisture of the scattered droplets is evaporated by hot air from the surface of the droplets, and solid particles are formed in the end. When the particle outer surface solidifies by rapid drying to form an outer shell, evaporation of water and contraction of the particles are considered to be inhibited to thereby lead to generation of hollow particles. In contrast, it is considered that drying of the particles and solidification of the entire particles simultaneously progress, without formation of a film as a particle outer shell, and generation of hollow particles is inhibited when the particles are dried after contraction. In other words, the balance between the drying rate and the contraction displacement is important. An appropriate combination of the various conditions described above is considered to enable the balance to be achieved. However, the factor is not limited thereto.

In spray-drying, a known spraying apparatus such as a rotating disk type, two-fluid nozzle type, or pressurized nozzle type can be used, for a method for converting the support precursor slurry into droplets.

The liquid to be sprayed is required to be used in a well-mixed state. If the liquid is in an insufficiently mixed state, the performance of the support is affected, such as decreased durability caused by uneven distribution of the composition. Particularly, on formulating the raw materials, increases in the slurry viscosity or partial gelling (colloidal condensation) may occur, resulting in a concern of formation of non-uniform particles. For this reason, in addition to taking into consideration gradually mixing the raw materials while stirring, for example, controlling the pH to a semi-stable region of the silica sol such as around pH 2 may be preferable by using a method such as adding acid or alkali.

The solid content of the liquid to be sprayed is preferably within a range of from 10 to 50% by mass is preferable in terms of the shape and particle diameter. As a measure for spray-drying conditions, the temperature at the outlet of the drying chamber of the spray dryer is preferably in a range of from 110 to 140° C. In the present embodiment, a spray drying apparatus having an inner diameter of 1000 mm or more may be used.

Next, the step (C) will be described. In the step (C), the dry powder obtained in the step (B) is calcined to obtain the support. The support calcining temperature is typically selected within a range of from 200 to 800° C. Calcining at a temperature above 800° C. is not preferable because the specific surface area tends to decrease considerably. The calcining atmosphere is not particularly limited, and calcining is typically carried out in air or nitrogen. The calcining time can be determined according to the specific surface area after calcining, and is generally from 1 to 48 hours. For calcining conditions, the porosity and other properties of the support may change, and thus selection of suitable temperature conditions and heating conditions is required. If the calcining temperature is excessively low, it tends to be difficult to maintain durability for a composite oxide, while if the calcining temperature is excessively high, there is the risk of causing decrease in the pore volume. The temperature rise conditions are preferably such that the temperature is raised gradually using programmed temperature rising or the like. A case of abrupt calcining under high temperature conditions is not preferable because gasification and combustion of inorganic substances and organic substances becomes violent, the support is exposed to a high-temperature state beyond the setting, and this exposure may cause the support to be pulverized.

From the viewpoints of ease of supporting composite particles, reaction activity in the case of using as a catalyst, difficulty in separation, and reaction activity, the specific surface area of the support is preferably 10 $m^2/g$ or more, more preferably 20 $m^2/g$ or more, and even more preferably 50 $m^2/g$ or more as measured by BET nitrogen adsorption. There is no particular limitations from the viewpoint of activity, but from the viewpoints of mechanical strength and water resistance, the specific surface area is preferably 700 $m^2/g$ or less, more preferably 350 $m^2/g$ or less, and even more preferably 300 $m^2/g$ or less.

If the pore diameter is smaller than 3 nm, the separation properties of the supported metal tend to be satisfactory, but in the case of using as a catalyst in a liquid phase reaction or the like, the pore diameter is preferably 3 nm or more from the viewpoints of not making the intrapore diffusion resistance excessively great so as not to cause the diffusion process of the reaction substrate to be rate-limiting as well as of maintaining the reaction activity at a high level. On the other hand, the pore diameter is preferably 50 nm or less from the viewpoints of difficulty in cracking of the supported material and difficulty in separation of the supported metal. Thus, the pore diameter of the support is preferably from 3 to 50 nm and more preferably from 3 to 30 nm. The pore volume is required for the presence of pores supporting composite nanoparticles. However, if the pore volume increases, the strength tends to suddenly decrease. Accordingly, from the viewpoints of strength and supporting characteristics, the pore volume is preferably within a range of from 0.1 to 1.0 mL/g and more preferably within a range of from 0.1 to 0.5 mL/g. The support of the present embodiment preferably satisfies the above ranges for both the pore diameter and pore volume.

The shape of the support depends on the reaction form. For a fixed bed reaction, a hollow cylindrical or honeycomb form, which results in little pressure loss, is selected. Under conditions of a liquid phase slurry suspension, generally chosen is a spherical form for which an optimum particle diameter is selected for use in accordance with the reactivity and the separation method. For example, in the case of employing a generally simple catalyst separation process based on precipitation separation, a particle diameter to be selected is preferably from 10 to 200 μm, more preferably from 20 to 150 μm, and even more preferably from 30 to 150 μm, in consideration of the balance with reaction characteristics. In the case of a cross filter system, small particles of 0.1 to 20 μm or less are preferable because of its higher reactivity. The type and form of the support can be changed according to the purpose of use for use in a catalyst for chemical synthesis.

The amount of oxidized nickel or cobalt supported on the support is not particularly limited, and is usually from 0.01 to 20% by mass, preferably from 0.1 to 10% by mass, more preferably from 0.2 to 5% by mass, and even more preferably from 0.5 to 2% by mass, as nickel or cobalt, based on the mass of the support. The amount of X supported on the support is usually from 0.01 to 10% by mass, preferably from 0.1 to 5% by mass, more preferably from 0.2 to 2% by mass, even more preferably from 0.3 to 1.5% by mass, and particularly preferably from 0.5 to 1.0% by mass, as metal, based on the mass of the support.

Moreover, in the present embodiment, a preferable range exists for the atomic ratio between nickel and/or cobalt and the above-mentioned constituent elements of the support. In the case of using the support composed of an aluminum-containing silica-based composition containing silica and alumina in the present embodiment, the compositional ratio between nickel or cobalt and alumina in a catalyst, in terms of the Ni/Al atomic ratio or the Co/Al atomic ratio, is preferably from 0.01 to 1.0, more preferably from 0.02 to 0.8, and even more preferably from 0.04 to 0.6. In the case of using a support containing silica, alumina, and an oxide of at least one basic metal of alkaline metals, alkaline earth metals, and rare earth metals, the compositional ratio between nickel or cobalt and alumina in the supported material, in terms of the atomic ratio of Ni/Al or the Co/Al atomic ratio, is preferably from 0.01 to 1.0, more preferably from 0.02 to 0.8, and even more preferably from 0.04 to 0.6, and the compositional ratio between nickel or cobalt and the basic metal component, in terms of the Ni/(alkaline metal+alkaline earth metal+rare earth metal) atomic ratio or the Co/(alkaline metal+alkaline earth metal+rare earth metal) atomic ratio, is preferably from 0.01 to 1.2, more preferably from 0.02 to 1.0, and even more preferably from 0.04 to 0.6.

When the atomic ratios of nickel and/or cobalt to aluminum and basic metal oxide as the support constituent elements are within the above ranges, the effects of improving elution of nickel and/or cobalt and structural changes in supported material particles tend to increase. This is thought to be because the nickel and/or cobalt, aluminum, and basic metal oxide form a specific composite oxide within the above ranges, thereby forming a stable bonding structure.

The catalyst for production of carboxylic acid ester of the present embodiment can contain a third constituent element, as an activity component, in addition to oxidized nickel and/or cobalt and X. Examples of third constituent elements that can be contained include titanium, vanadium, chromium, manganese, iron, zinc, gallium, zirconium, niobium, molybdenum, rhodium, cadmium, indium, tin, antimony, tellurium, hafnium, tantalum, tungsten, rhenium, osmium, iridium, mercury, thallium, lead, bismuth, aluminum, boron, silicon, and phosphorous. The content of these third constituent elements is preferably from 0.01 to 20% by mass and more preferably from 0.05 to 10% by mass in the supported material. At least one metal component selected from alkaline metals, alkaline earth metals, and rare earth metals may also be contained in the catalyst for production of carboxylic acid ester. The content of the alkaline metal, alkaline earth metal, or rare earth metal is preferably selected to be within a range of 15% by mass or less in the supported material.

These third constituent elements or alkaline metal, alkaline earth metal and rare earth metal may be contained in the supported material during production or reaction of the catalyst for production of carboxylic acid ester, or a method may be used in which these are contained in the support in advance.

The specific surface area of the catalyst for production of carboxylic acid ester of the present embodiment is preferably within a range of from 20 to 350 $m^2/g$, more preferably from 50 to 300 $m^2/g$, and even more preferably from 100 to 250 $m^2/g$, as measured by BET nitrogen adsorption, from the viewpoints of reaction activity and resistance to separation of active components.

The pore diameter of the catalyst for production of carboxylic acid ester is originating from the pore structure of the support. If the pore diameter is smaller than 3 nm, the separation properties of the supported metal component tend to be satisfactory. However, in the case of using as a catalyst in a liquid phase reaction or the like, the pore diameter is preferably 3 nm or more, from the viewpoints of not making the intrapore diffusion resistance excessively large so as not to cause the diffusion process of the reaction substrate to be rate-limiting as well as of maintaining the reaction activity at a high level. On the other hand, the pore diameter is preferably 50 nm or less from the viewpoints of difficulty in cracking of the supported material and difficulty in separation of the supported composite particles. Thus, the pore diameter of the catalyst for production of carboxylic acid ester is preferably from 3 to 50 nm, more preferably from 3 to 30 nm, and even more preferably from 3 to 10 nm. From the viewpoints of supporting characteristics and reaction characteristics, the pore volume is preferably within a range of from 0.1 to 1.0 mL/g, more preferably from 0.1 to 0.5 mL/g, and even more preferably from 0.1 to 0.3 mL/g. The catalyst for production of carboxylic acid ester of the present embodiment preferably satisfies the above ranges for both the pore diameter and pore volume.

[Method for Producing Catalyst for Production of Carboxylic Acid Ester]

The method for producing a catalyst for production of carboxylic acid ester of the present embodiment is not particularly limited and can include the following preferable steps. In other words, the method for producing a catalyst for production of carboxylic acid ester preferably includes a step (A) of preparing a support precursor slurry comprising raw material for the support, the slurry being at a temperature of 5° C. or more and 60° C. or less and having a viscosity of 10 cp or more and 550 cp or less, a step (B) of supplying the support precursor slurry to a spray dryer to spray-dry the support precursor slurry at an inlet temperature of the spray dryer of 150° C. or more and 215° C. or less, a step (C) of calcining the spray-dried precursor slurry after the step (B) to obtain a support, and a step (D) of allowing the support to support the catalyst metal particles. The steps (A) to (C) are as described above, and the step (D) will be described hereinafter.

In the step (D), the support is allowed to support the catalyst metal particles. In a first sub-step, an aqueous slurry containing a support supporting an oxide of at least one basic metal selected from the group consisting of alkaline metals, alkaline earth metals, and rare earth metals is mixed with an acidic aqueous solution of soluble metal salts containing nickel and/or cobalt and X (wherein X represents at least one element selected from the group consisting of nickel, palladium, platinum, ruthenium, gold, silver and copper). The temperature of the mixture of both liquids is adjusted so as to be 60° C. or more. A precursor of a catalyst for production of carboxylic acid ester in which the nickel and/or cobalt and X component have precipitated on the support is formed in the mixture.

Next, in a second sub-step, the precursor obtained in the first sub-step is washed with water and dried as necessary followed by subjecting to heat treatment, and thus the catalyst for production of carboxylic acid ester can be obtained.

According to this method, a catalyst for production of carboxylic acid ester can be obtained that has a supported layer in which the composite particles are localized but does not contain composite particles in a region that includes the center of the support.

In the present embodiment, prior to the first sub-step, it is preferable to carry out an aging step of aging, in water, the support supporting an oxide of at least one basic metal selected from the group consisting of alkaline metals, alkaline earth metals, and rare earth metals. Aging the support in advance allows a layer having a sharp distribution of composite particles to be obtained. The effect caused by aging the support is presumed, based on the results of measuring pore distribution by nitrogen adsorption, to be attributable to a more uniform and sharper pore structure due to occurrence of realignment of the pore structure of the support. Although the aging can be carried out at room temperature, the aging temperature for the support is preferably selected within a range of from 60 to 150° C., which is higher than room temperature, because the pore structure changes slowly. In the case in which the aging is carried out at normal pressure, a temperature within a range of from 60 to 100° C. is preferable. The duration of the aging treatment varies according to the temperature conditions. In the case of 90° C., for example, the duration is preferably from 1 minute to 5 hours, more preferably from 1 to 60 minutes, and even more preferably from 1 to 30 minutes. In the operation of the first sub-step, although the support can be used after aged, then once dried, and calcined, a slurry obtained by dispersing the support in water is preferably brought into contact with the acidic aqueous solution of soluble metal salts containing nickel and/or cobalt and X followed by insoluble immobilization of the nickel and/or cobalt and X on the support.

Examples of soluble metal salts containing nickel for use in preparation of a catalyst include nickel nitrate, nickel acetate, and nickel chloride. Examples of soluble metal salts containing X include palladium chloride and palladium acetate in the case of selecting palladium for X, ruthenium chloride and ruthenium nitrate in the case of selecting ruthenium for X, chloroauric acid, sodium tetrachloroaurate, potassium dicyanoaurate, gold diethylamine trichloride, and gold cyanide in the case of selecting gold for X, and silver chloride and silver nitrate in the case of selecting silver for X.

The concentration of each of the aqueous solutions containing nickel and/or cobalt and X are usually within a range of from 0.0001 to 1.0 mol/L, preferably from 0.001 to 0.5 mol/L, and more preferably from 0.005 to 0.2 mol/L. The ratio of nickel or cobalt to X in the aqueous solutions, as the Ni/X atomic ratio or the Co/X atomic ratio, is preferably within a range of from 0.1 to 10, more preferably from 0.2 to 5.0, and even more preferably from 0.5 to 3.0.

The temperature during contact between the support and the acidic aqueous solution of soluble metal salts containing nickel and/or cobalt and X is one important factor for controlling the distribution of composite particles, and varies according to the amount of the oxide of at least one basic metal selected from the group consisting of alkaline metals, alkaline earth metals, and rare earth metals supported in advance on the support. If the temperature is excessively low, the reaction slows, and the distribution of the composite particles tends to widen. In the production method of the present embodiment, from the viewpoint of obtaining a supported layer in which the composite particles are more sharply localized, the temperature during contact with the acidic aqueous solution of soluble metal salts containing nickel and/or cobalt and X is a temperature at which a high reaction rate is achieved, and is preferably 60° C. or more, more preferably 70° C. or more, even more preferably 80° C. or more, and particularly preferably 90° C. or more. Since the acidic aqueous solution and the aqueous slurry may be mixed so that the temperature of the mixed liquid thereof is 60° C. or more, the aqueous slurry may be heated to a degree such that the mixed liquid exceeds 60° C. even after the acidic aqueous solution is added, or conversely only the acidic aqueous solution may be heated. Both the acidic aqueous solution and the aqueous slurry may naturally also be heated to 60° C. or more.

The reaction can be carried out under applied pressure at a temperature equal to or higher than the boiling point of the solution, and usually preferably carried out at a temperature equal to or lower than the boiling point for the ease of the operation. The duration of immobilization of the nickel and/or cobalt and X components is not particularly limited, and depends on conditions such as the type of support, the amount of nickel and/or cobalt and X supported and the ratio thereof. The duration is usually within a range of from 1 minute to 5 hours, preferably from 5 minutes to 3 hours, and more preferably from 5 minutes to 1 hour.

The method for producing a catalyst for production of carboxylic acid ester of the present embodiment is based on the principle of insoluble immobilization of the nickel and/or cobalt and X component by carrying out a chemical reaction between an oxide of at least one basic metal selected from the group consisting of alkaline metals, alkaline earth metals, and rare earth metals supported in advance on the support and soluble metal salts containing nickel and/or cobalt and X. In order to ensure more sufficient compounding of the nickel and/or cobalt and X component, both the components are preferably immobilized simultaneously from a mixed solution containing both the components.

In the production method of the present embodiment, the aqueous slurry containing a support supporting an oxide of at least one basic metal selected from the group consisting of alkaline metals, alkaline earth metals, and rare earth metals preferably contains a salt of at least one basic metal selected from the group consisting of alkaline metals, alkaline earth metals, and rare earth metals.

Thus, formation of metal black of X can be inhibited, compounding of nickel and/or cobalt and X is facilitated, and the distribution of composite particles can be controlled more precisely. Such effects are presumed to be caused by controlling the rate of the chemical reaction between the basic metal oxide supported in advance on the support and the soluble metal salts containing nickel and/or cobalt and X by means of addition of a salt of at least one metal selected from the group consisting of alkaline metals, alkaline earth metals and rare earth metals to the aqueous solution.

Examples of salts of at least one basic metal selected from the group consisting of alkaline metals, alkaline earth metals, and rare earth metals that can be used include one or more selected from water-soluble salts of these metals such as organic acid salts, and inorganic salts including nitrates and chlorides.

The amount of the salt of at least one basic metal selected from the group consisting of alkaline metals, alkaline earth metals, and rare earth metals described above varies according to the amounts and ratio of the nickel and/or cobalt and X component, and is determined according to the amount of the basic metal oxide supported in advance on the support. Usually, the amount of the salt is from 0.001 to 2 times moles and preferably from 0.005 to 1 time moles based on the amount of the nickel and/or cobalt and X component in the aqueous solution.

The aqueous slurry containing a support supporting an oxide of at least one basic metal selected from the group consisting of alkaline metals, alkaline earth metals, and rare earth metals preferably contains a soluble aluminum salt. Examples of soluble aluminum salts that can be used include aluminum chloride and aluminum nitrate.

Addition of a soluble aluminum salt to the aqueous slurry can lead to formation of an outer layer substantially free of composite particles on the outside of the supported layer in which the composite particles are localized. This is also based on the principle of insoluble immobilization as described above. A soluble salt such as aluminum chloride or aluminum nitrate is used for the soluble aluminum salt. Aluminum is allowed to react on the outer surface of the support by a chemical reaction with the basic metal oxide supported in advance on the support, the reaction field for nickel and/or cobalt and X is consumed, and the basic metal oxide further inside and the nickel and/or cobalt and X are immobilized by a reaction.

The amount of the aluminum component varies according to the setting of the thickness (μm) of the layer not supporting the nickel and/or cobalt and X component thereon, and is determined according to the amount of the basic metal oxide supported in advance on the support. Usually, the amount of the aluminum component is from 0.001 to 2 times moles and preferably from 0.005 to 1 time mole based on the amount of the basic metal oxide supported in advance on the support.

Although much is still unknown about the details of the mechanism by which the nickel and/or cobalt and X component are distributed, it is presumed that the diffusion rate of the nickel and/or cobalt and X-containing soluble component in the support and the rate at which the components are insolubilized by a chemical reaction were well-balanced under the conditions of the present embodiment, thereby enabling the composite particles to be immobilized in a narrow region near the surface of the support.

In the case of forming an outer layer substantially free of composite particles on the outer surface of the support, aluminum and a basic metal component near the outer surface of the support are allowed to react with each other to lead to consumption of the basic metal component that may react with the nickel and/or cobalt and X component near the outer surface of the support, and when nickel and/or cobalt and X are subsequently supported, the reactive basic metal component near the outer surface of the support is already consumed. Accordingly, the nickel and/or cobalt and X are presumed to react with the basic metal oxide inside the support followed by being immobilized.

Next, the second sub-step will be described.

The first precursor is washed with water and dried as necessary prior to the heat treatment of the second sub-step. The heating temperature for the first precursor is usually from 40 to 900° C., preferably from 80 to 800° C., more preferably from 200 to 700° C., and even more preferably from 300 to 600° C.

The heat treatment is carried out in an atmosphere such as air (or atmospheric air), an oxidizing atmosphere (such as oxygen, ozone, nitrogen oxides, carbon dioxide, hydrogen peroxide, hypochlorous acid, or inorganic or organic peroxide), or an inert gas atmosphere (such as helium, argon, or nitrogen). The heating time is only required to be suitably selected according to the heating temperature and the amount of the first precursor. The heat treatment can be carried out at normal pressure, under applied pressure, or under reduced pressure.

Following the second sub-step described above, a reduction treatment can be carried out in a reducing atmosphere (such as hydrogen, hydrazine, formalin, or formic acid) as necessary. In this case, a treatment method selected and carried out in which the oxidized nickel and/or cobalt are not completely reduced to a metallic state. The temperature and duration of the reducing treatment are suitably selected according to the type of the reducing agent, the type of X, and the amount of the catalyst.

Further, following the above-mentioned heat treatment or reducing treatment, oxidizing treatment can be carried out in air (or atmospheric air) or an oxidizing atmosphere (such as oxygen, ozone, nitrogen oxide, carbon dioxide, hydrogen peroxide, hypochlorous acid, or inorganic or organic peroxide), as necessary. The temperature and duration in this case is suitably selected according to the type of the oxidizing agent, the type of X, and the amount of the catalyst.

A third constituent element other than nickel and/or cobalt and X can be added during preparation of the supported material or under reaction conditions. The alkaline metal, alkaline earth metal, or rare earth metal can also be added during catalyst preparation or to the reaction system. The raw materials for the third constituent element, alkaline metal, alkaline earth metal, and rare earth metal are selected from salts of organic acids, salts of inorganic acids, hydroxides, and the like.

[Method for Producing Carboxylic Acid Ester]

The catalyst for production of carboxylic acid ester of the present embodiment can be widely used as a catalyst for chemical synthesis. For example, the catalyst can be used in reactions for forming carboxylic acid esters from aldehydes and alcohols and reactions for forming carboxylic acid esters from alcohols. In other words, the method for producing carboxylic acid ester of the present embodiment can include a step of carrying out a reaction of (a) an aldehyde and an alcohol or of (b) one or two or more alcohols in the presence of the catalyst for production of carboxylic acid ester of the present embodiment and oxygen.

The catalyst for production of carboxylic acid ester of the present embodiment exerts excellent effects particularly when used as a catalyst for oxidization reactions. In addition to the aldehydes and alcohols used in the reaction for forming carboxylic acid ester as indicated in the examples, examples of reaction substrates used in the present embodiment include various reaction substrates such as alkanes, olefins, alcohols, ketones, aldehydes, ethers, aromatic compounds, phenols, sulfur compounds, phosphorous compounds, oxygen-containing nitrogen compounds, amines, carbon monoxide, and water. These reaction substrates can be used singly or as a mixture composed of two or more thereof. Various industrially useful oxidation products such as oxygen-containing compounds, oxidative adducts, and oxidative dehydrogenation products are obtained from these reaction substrates.

As specific reaction substrates, examples of alkanes include aliphatic alkanes such as methane, ethane, propane, n-butane, isobutane, n-pentane, n-hexane, 2-methylpentane, and 3-methylpentane, and alicyclic alkanes such as cyclopentane, cyclohexane, cycloheptane, and cyclooctane.

Examples of olefins include aliphatic olefins such as ethylene, propylene, butene, pentene, hexene, heptene, octene, decene, 3-methyl-1-butene, 2,3-dimethyl-1-butene, and allyl chloride; alicyclic olefins such as cyclopentene, cyclohexene, cycloheptene, cyclooctene, and cyclodecene; and aromatic substituted olefins such as styrene and α-methylstyrene.

Examples of alcohols include saturated and unsaturated aliphatic alcohols such as methanol, ethanol, n-propanol, isopropanol, n-butanol, s-butanol, t-butanol, n-pentanol, n-hexanol, n-heptanol, allyl alcohol, and crotyl alcohol; saturated and unsaturated alicyclic alcohols such as cyclopentanol, cyclohexanol, cycloheptanol, methylcyclohexanol, and cyclohexen-1-ol; aliphatic and alicyclic polyhydric alcohols such as ethylene glycol, propylene glycol, trimethylene glycol, 1,3-butanediol, 1,2-cyclohexanediol, and 1,4-cyclohexanediol; and aromatic alcohols such as benzyl alcohol, salicyl alcohol, and benzhydrol.

Examples of aldehydes include aliphatic saturated aldehydes such as formaldehyde, acetoaldehyde, propionaldehyde, isobutylaldehyde, and glyoxal; aliphatic α,β-unsaturated aldehydes such as acrolein, methacrolein, and crotonaldehyde; aromatic aldehydes such as benzaldehyde, tolylaldehyde, benzylaldehyde, and phthalaldehyde; and derivatives of these aldehydes.

Examples of ketones include aliphatic ketones such as acetone, methyl ethyl ketone, diethyl ketone, dipropyl ketone, and methyl propyl ketone; alicyclic ketones such as cyclopentanone, cyclohexanone, cyclooctanone, 2-methylcyclohexanone, and 2-ethylcyclohexanone; and aromatic ketones such as acetophenone, propiophenone, and benzophenone.

Examples of aromatic compounds include benzene, toluene, xylene, naphthalene, anthracene, or derivatives thereof obtained by substitution with an alkyl group, an aryl group, a halogen, a sulfone group, or the like.

Examples of phenols include phenol, cresol, xylenol, naphthol, anthrol (hydroxyanthracene), and derivatives thereof (such as those obtained by replacing a hydrogen atom in the aromatic ring with an alkyl group, an aryl group, a halogen atom, a sulfonic acid group, or the like).

Examples of sulfur compounds include mercaptans such as methyl mercaptan, ethyl mercaptan, propyl mercaptan, benzyl mercaptan, and thiophenol.

Examples of amines include aliphatic amines such as methylamine, ethylamine, propylamine, isopropylamine, butylamine, dimethylamine, diethylamine, dipropylamine, diisopropylamine, dibutylamine, trimethylamine, triethylamine, tripropylamine, tributylamine, allylamine, and diallylamine; alicyclic amines such as cyclopentylamine, cyclohexylamine, cycloheptylamine, and cyclooctylamine; and aromatic amines such as aniline, benzylamine, and toluidine.

These reaction substrates can be used singly or as a mixture composed of two or more thereof. The reaction substrates are not necessarily required to be purified, and may be in a form of mixture with other organic compounds.

Hereinafter, a method for producing carboxylic acid ester from an aldehyde and an alcohol in the presence of oxygen by an oxidative esterification reaction using the catalyst for production of carboxylic acid ester of the present embodiment will be described by way of example.

Examples of the aldehyde used as a raw material include $C_1$ to $C_{10}$ aliphatic saturated aldehydes such as formaldehyde, acetoaldehyde, propionaldehyde, isobutylaldehyde, and glyoxal; $C_3$ to $C_{10}$ alicyclic α,β-unsaturated aldehydes such as acrolein, methacrolein, and crotonaldehyde; $C_6$ to $C_{20}$ aromatic aldehydes such as benzaldehyde, tolylaldehyde, benzylaldehyde, and phthalaldehyde; and derivatives of these aldehydes. These aldehydes can be used singly or as a mixture of any two or more thereof. In the present embodiment, the aldehyde is preferably selected from acrolein, methacrolein, or a mixture of these.

Examples of alcohols include $C_1$ to $C_{10}$ aliphatic saturated alcohols such as methanol, ethanol, isopropanol, butanol, 2-ethylhexanol, and octanol; $C_5$ to $C_{10}$ alicyclic alcohols such as cyclopentanol and cyclohexanol; $C_2$ to $C_{10}$ diols such as ethylene glycol, propylene glycol, and butanediol; $C_3$ to $C_{10}$ aliphatic unsaturated alcohols such as allyl alcohol and methallyl alcohol; $C_6$ to $C_{20}$ aromatic alcohols such as benzyl alcohol; and hydroxyoxetanes such as 3-alkyl-3-hydroxymethyloxetane. These alcohols can be used singly or as a mixture of any two or more thereof. In the present embodiment, it is preferable that the aldehyde be acrolein and/or methacrolein and the alcohol be methanol.

In the present embodiment, from the viewpoint of further improving reaction results, the moisture content in the alcohol is preferably 10% by mass or less, more preferably 0.01% by mass or more and 10% by mass or less, more preferably 7% by mass or less, even more preferably 5% by mass or less, and still even more preferably 1% by mass or less.

A smaller moisture content in the alcohol is preferable, and thus the lower limit value is not particularly limited. For example, the moisture content may be 0.01% by mass or may be a value smaller than this value.

The amount ratio of the aldehyde to the alcohol is not particularly limited, and the reaction can be carried out over a wide range of a molar ratio of aldehyde/alcohol of from 10 to 1/1,000. The reaction is generally carried out within the range of a molar ratio of from 2/100 to 50/100 and preferably carried out within the range of a molar ratio of from 20/100 to 50/100.

The total amount of the aldehyde and the alcohol in the reaction is not particularly limited, and may be, for example, 80% by mass or more and may be 90% by mass or more based on the total mass of the liquid components.

The amount of catalyst used can be varied considerably according to the types of reaction raw materials, the composition of the catalyst, preparation method, reaction conditions and reaction form, and the like and is not particularly limited. In the case of allowing the catalyst to react in a slurry form, the amount of catalyst used, in terms of the solid content in the slurry, is preferably within the range of from 1 to 50 mass/vol %, more preferably from 3 to 30 mass/vol %, and even more preferably from 10 to 25 mass/vol %.

The production of carboxylic acid ester may be carried out by any method such as a vapor phase reaction, liquid phase reaction, or irrigation liquid reaction, and a liquid phase reaction is preferable.

The method for producing carboxylic acid ester of the present embodiment can be carried out as a batch or continuous process, and a continuous process is preferable.

The reaction can be carried out in the absence of solvent, and can also be carried out using a solvent that is inert to the reaction components such as hexane, decane, benzene, dioxane, or the like.

The reaction can be carried out by means of a conventionally known form, such as a fixed bed form, a fluid bed form, or a stirred tank form. For example, when carried out in the liquid phase, the reaction can be carried out by means of any form of reaction vessel, such as a bubble column reactor, a draft tube reactor, or a stirred tank reactor. When a stirred tank reactor is used, the tip speed of the stirring blade may be in the range of from 1 to 20 m/s, for example.

The oxygen used to produce carboxylic acid ester can be molecular oxygen, that is, can be in the form of oxygen gas itself or a mixed gas in which oxygen gas has been diluted with a diluent inert to the reaction such as nitrogen or carbon dioxide gas. Air is preferably used for the oxygen raw material from the viewpoints of ease of manipulation, economy, and the like.

The oxygen partial pressure varies according to the reaction raw materials such as the type of aldehyde or type of alcohol, the reaction conditions or the type of reactor, and the like. The oxygen partial pressure at the reactor outlet is practically within the range equal to or lower than the lower limit of the explosive range, and is preferably controlled to, for example, from 20 to 80 kPa. The reaction can be carried out at a reaction pressure within a wide pressure range from reduced pressure to applied pressure, and is usually carried out at a pressure within the range of from 0.05 to 2 MPa. From the viewpoint of safety, the total pressure is preferably set such that the oxygen concentration of the reactor outflow gas does not exceed the explosive limit (e.g., an oxygen concentration of 8 vol %).

In the case of carrying out the production reaction of carboxylic acid ester in a liquid phase or the like, the pH of the reaction system is preferably maintained at from 6 to 9 by adding a compound of an alkaline metal or alkaline earth metal (e.g., an oxide, hydroxide, carbonate, or carboxylate) to the reaction system. These alkaline metal or alkaline earth metal compounds can be used singly or in combination of two or more thereof.

The reaction can be carried out even at a high temperature of 200° C. or more, and the reaction temperature during production of carboxylic acid ester is preferably from 30 to 200° C., more preferably from 40 to 150° C., and even more preferably from 60 to 120° C. The reaction time is not particularly limited, cannot be determined unconditionally because of varying according to the set conditions, and is usually from 1 to 20 hours.

EXAMPLES

The present embodiment will be now further described with reference to the following examples, but the present embodiment is not limited to the examples in any way.

In the following examples and comparative examples, various physical properties were measured in accordance with the following methods.

[Determination of Amount of Catalyst Metal Particles Supported, Amount of Element (Such as Ni/(Ni+X) Atomic Ratio), and Content of Support]

The amount of catalyst metal particles supported and the concentration of elements contained in the support (e.g., Ni, Co, and X) were quantified using an ICP emission analyzer (ICP-AES, MS), "IRIS Intrepid II Model XDL" (trade name) manufactured by Thermo Fisher Scientific K.K.

Samples were prepared as described below. First, a silica-based material was weighed into a Teflon® decomposition vessel, and nitric acid and hydrogen fluoride were added thereto. The resulting solution was heated and decomposed in a microwave decomposer, "ETHOS Model TC" (trade name) manufactured by Milestone General followed by evaporating to dryness over a heater. Then, nitric acid and hydrochloric acid were added to the precipitated residue, and the mixture was decomposed under applied pressure. Pure water was added to the resulting decomposition liquid to make a predetermined volume, and this solution was used as the sample.

Quantification of the samples was carried out by an internal standard method in the ICP-AES. The amount of the catalyst metal particles supported and the content of elements contained in the support were determined by subtracting a simultaneously determined operation blank value, and the amount supported and the constitution concentration were calculated. The content of the support was a value obtained by subtracting the amount supported (% by mass) from 100% by mass.

[Shape Observation of Support and Catalyst Particles]

The support and catalyst particles were observed using an X-650 scanning electron microscope (SEM) manufactured by Hitachi, Ltd.

[Hollow Particle Ratio]

Cross sections of catalyst particles were observed, the number of hollow particles was counted, and the hollow particle ratio was determined in the following manner.

For observation with an electron microscope, #02-1001 Oken Epok 812 set (embedding resin for microscope) manufactured by Okenshoji Co., Ltd. was used. The procedure for mixing the embedding resin and catalyst particles were as follows. That is, EPOK 812 (DENACOL EX-314, Nagase ChemteX Corporation) and DDSA (DSA, Sanyo Chemical Industries, Ltd.) were mixed for 10 minutes, and then MNA (KAYAHA RD MCD, NIPPON KAYAKU Co., Ltd.) was added thereto and mixed for 10 minutes. Further, DMP-30 (SEIKUOL TDMP, manufactured by Seiko Chemical Co., Ltd.) was added thereto and mixed for 10 minutes, and then vacuum deaeration was carried out for one hour to expel dissolved air contained. After the vacuum deaeration, calcined catalyst particles was added to the resin and mixed. The mixture was poured into a silicone embedding board (manufactured by D.S.K DOSAKA EM CO., LTD.), left to settle for about 30 minutes, and then cured using a dryer at 60° C. for 12 hours to thereby obtain a cured product of the embedding resin including the catalyst particles embedded therein.

Then, a flat cross section of the cured product was formed on a polisher by use of 1.0 μm alumina as a polishing agent to expose the cross section of the catalyst particles. Subsequently, the polished cured product was bonded to the sample stage with carbon tape and subjected to conductive treatment by deposition of osmium to obtain a sample for observation.

The cross section of the sample for observation was observed under the following conditions, using an Ultra-high-resolution analytical scanning electron microscope SU-70 manufactured by Hitachi High-Technologies Corporation. Here, the cross section was imaged at a magnification of 100 times, and images were obtained until the total number of particles that were spherical and of which the particle cross section was observable reached 1500 or more. The images were obtained as reflected electron images using a YAG detector at an acceleration voltage of 20 kV. The distance between the electron lens and the sample for observation (working distance) was set to 15 mm. Here, one particle having an area occupied by voids inside the particle of 1% or more with respect to the cross-sectional area of the particle was determined as a hollow particle. Cracks of particles were excluded from the voids in judgment on hollow particles. Pores having a pore diameter of 100 nm or less formed on the particle surface were excluded from the area occupied by voids inside the particle.

The total number of the particles in the imaged images and the number of the hollow particles were counted. The hollow particle ratio was calculated by dividing the number of the hollow particles by the total number of the particles and multiplying the resultant by 100.

<Conditions>

Acceleration voltage: 20 kV
Observation mode: reflected electron image (YAG)
W.D. (working distance): 15 mm
Objective lens: normal mode
Movable aperture: objective: 3, anode: 4

Example 1

An aqueous solution obtained by dissolving aluminum nitrate, magnesium nitrate, and 540 g of a 60% by mass nitric acid in 5.0 L of pure water such that the amounts of aluminum and magnesium to be contained in a support would be 8.3 mol % and 8.3 mol % respectively, with respect to the total molar amount of silicon, aluminum, and magnesium was gradually added dropwise into 20.0 kg of a solution of a silica sol having a colloidal particle diameter of from 10 to 20 nm (manufactured by Nissan Chemical Corporation, SNOWTEX N-30, $SiO_2$ content: 30% by mass) in a stirred state maintained at 15° C. to obtain a mixed slurry of the silica sol, aluminum nitrate, and magnesium nitrate. Thereafter, the mixed slurry was maintained at 55° C. for 30 hours while stirred at 550 rpm. The viscosity of the mixed slurry at this time (under 55° C.) was 139 cp. This mixed slurry was spray-dried with a spray dryer (inner diameter: 1600 mm) set to an inlet temperature at 190° C. to obtain a solid.

Then, the resulting solid was filled to a thickness of about 1 cm into a stainless steel container having an open top, heated in an electric furnace from room temperature to 300° C. over 2 hours, and thereafter held for 3 hours. Further, after heated to 800° C. over 2 hours and held for 3 hours, the solid was cooled to obtain a support. The average particle diameter of the support was 64 μm based on the results of measurement of laser diffraction/scattering particle size distribution. The form of the support was determined to be nearly spherical based on observations using a scanning electron microscope (SEM).

Next, 1.0 L of an aqueous solution containing 16.35 g of nickel nitrate hexahydrate and 13 mL of a 1.3 mol/L aqueous chloroauric acid solution was heated to 90° C. 300 g of the silica-alumina-magnesia support obtained above was added to this aqueous solution and stirred for one hour while held at 90° C. under stirring to thereby precipitate the nickel and gold component onto the support.

Then, after removing the supernatant by allowing to stand and washing several times with distilled water, the washed resultant was filtered. This filtered residue was dried at 105° C. for 16 hours and calcined at 500° C. in air for 3 hours to obtain a catalyst supporting 1.0% by mass nickel and 0.90% by mass gold (NiOAu/$SiO_2$—$Al_2O_3$—MgO, amount of aluminum with respect to the total molar amount of silicon and aluminum: 9 mol %, Mg/Al atomic ratio: 0.5). That is, the content of the support in the catalyst was 98.1% by mass. The Ni/(Ni+Au) atomic ratio of the resulting catalyst was 0.77. The average particle diameter of the catalyst was 65 μm based on the results of measurement of laser diffraction/scattering particle size distribution. The hollow particle ratio of this catalyst was 23%.

240 g of the catalyst (NiOAu/$SiO_2$—$Al_2O_3$—MgO) was placed into a stirred stainless steel reactor having a liquid phase portion of 1.2 liters followed by carrying out an oxidative carboxylic acid ester formation reaction (liquid phase reaction) from an aldehyde and an alcohol or one or two or more alcohols while stirring the contents at a tip speed of the stirrer blade of 4 m/s. A solution of 36.7% by mass methacrolein in methanol (aldehyde/alcohol molar ratio=26.5/100) at 0.6 liters/hr and a solution of 1 to 4% by mass NaOH in methanol at 0.06 liters/hr were continuously supplied to the reactor, air was blown in at a reaction temperature of 80° C. and a reaction pressure of 0.5 MPa such that the outlet oxygen concentration was 4.0 vol % (equivalent to the oxygen partial pressure of 0.02 MPa), and the concentration of NaOH supplied to the reactor was controlled such that a pH of the reaction system was 7. The reaction product was continuously extracted from the reactor outlet by overflow, and the reactivity was investigated by analyzing by gas chromatography.

At 300 hours after the start of the reaction, the methacrolein conversion rate was 65.3%, and the selectivity of methyl methacrylate was 95.2%. The catalyst after reaction of 300 hours was sieved using a sieve having an aperture of 32 μm, and the mass thereof was determined. The proportion of particles larger than 32 μm was 98% by mass.

Various conditions for the catalyst production and the results of the hollow particle ratio and reaction results are also shown in Table 1.

Example 2

A catalyst was prepared in the same manner as in Example 1 except that the inlet temperature was set to 160° C. during spray-drying with a spray dryer, and the hollow particle ratio and reaction results were determined in the same manner as in Example 1. Various conditions for the catalyst production and various measurement results are shown in Table 1.

Example 3

A catalyst was prepared in the same manner as in Example 1 except that 540 g of 60% nitric acid was dissolved in 12.0 L of pure water and that a mixed slurry of a silica sol, aluminum nitrate, and magnesium nitrate was held at 40° C. for 30 hours while stirred at 600 rpm, and the hollow particle ratio and reaction results were determined in the same manner as in Example 1. Various conditions for the catalyst production and various measurement results are shown in Table 1.

Example 4

A catalyst was prepared in the same manner as in Example 1 except that a mixed slurry of a silica sol, aluminum nitrate, and magnesium nitrate was held at 15° C. for 30 hours while stirred at 450 rpm, and the hollow particle ratio and reaction results were determined in the same manner as in Example 1. Various conditions for the catalyst production and various measurement results are shown in Table 1.

Example 5

A catalyst was prepared in the same manner as in Example 1 except that the inlet temperature was set to 205° C. during spray-drying with a spray dryer, and the hollow particle ratio and reaction results were determined in the same manner as in Example 1. Various conditions for the catalyst production and various measurement results are shown in Table 1.

Example 6

A catalyst was prepared in the same manner as in Example 1 except that 540 g of 60% nitric acid was dissolved in 3.0 L of pure water, that a mixed slurry of a silica sol, aluminum nitrate, and magnesium nitrate was held at 5° C. for 30 hours while stirred at 550 rpm, and that the inlet temperature was set to 185° C. during spray-drying with a spray dryer, and the hollow particle ratio and reaction results were determined in the same manner as in Example 1. Various conditions for the catalyst production and various measurement results are shown in Table 1.

Example 7

A catalyst was prepared in the same manner as in Example 1 except that a mixed slurry of a silica sol, aluminum nitrate, and magnesium nitrate was stirred at 160 rpm, and the hollow particle ratio and reaction results were determined in the same manner as in Example 1. Various conditions for the catalyst production and various measurement results are shown in Table 1.

Example 8

A catalyst was prepared in the same manner as in Example 1 except that a mixed slurry of a silica sol, aluminum nitrate, and magnesium nitrate was held at 40° C. for 30 hours while stirred at 340 rpm, and the hollow particle ratio and reaction results were determined in the same manner as in Example 1. Various conditions for the catalyst production and various measurement results are shown in Table 1.

Comparative Example 1

A catalyst was prepared in the same manner as in Example 1 except that a mixed slurry of a silica sol, aluminum nitrate, and magnesium nitrate was held at 70° C. for 30 hours, and the particle proportion and reaction results were determined in the same manner as in Example 1. Various conditions for the catalyst production and various measurement results are shown in Table 1.

Comparative Example 2

A catalyst was prepared in the same manner as in Example 1 except that a mixed slurry of a silica sol, aluminum nitrate, and magnesium nitrate was stirred at 650 rpm, and the hollow particle ratio and reaction results were determined in the same manner as in Example 1. Various conditions for the catalyst production and various measurement results are shown in Table 1.

Comparative Example 3

A catalyst was prepared in the same manner as in Example 1 except that a mixed slurry of a silica sol, aluminum nitrate, and magnesium nitrate was stirred at 100 rpm, and the hollow particle ratio and reaction results were determined in the same manner as in Example 1. Various conditions for the catalyst production and various measurement results are shown in Table 1.

Comparative Example 4

A catalyst was prepared in the same manner as in Example 1 except that the inlet temperature was set to 225° C. during spray-drying with a spray dryer, and the hollow particle ratio and reaction results were determined in the same manner as in Example 1. Various conditions for the catalyst production and various measurement results are shown in Table 1.

Comparative Example 5

Preparation of a support was attempted in the same manner as in Example 7 except that aluminum nitrate, magnesium nitrate, and 540 g of 60% by mass nitric acid were dissolved in 2.0 L of pure water, but spray-drying with a spray dryer could not be conducted, and the support could not be obtained. The results are shown in Table 1.

TABLE 1

| | Slurry temperature [° C.] | Slurry viscosity [cp] | Spray dryer inlet temperature [° C.] | Stirring rotational speed [rpm] | Hollow particle ratio [%] | Methacrolein conversion rate [%]/MMA selectivity [%] |
|---|---|---|---|---|---|---|
| Example 1 | 55 | 139 | 190 | 550 | 23 | 65.3/95.2 |
| Example 2 | 55 | 139 | 160 | 550 | 26 | 65.1/95.1 |
| Example 3 | 40 | 51 | 190 | 600 | 31 | 64.9/94.8 |
| Example 4 | 15 | 478 | 190 | 450 | 33 | 64.5/94.7 |
| Example 5 | 55 | 139 | 205 | 550 | 38 | 63.8/94.1 |
| Example 6 | 5 | 521 | 185 | 550 | 39 | 63.5/93.8 |
| Example 7 | 55 | 207 | 190 | 160 | 35 | 64.6/94.6 |
| Example 8 | 40 | 156 | 190 | 340 | 36 | 64.6/94.2 |
| Comparative Example 1 | 70 | 8 | 190 | 550 | 51 | 62.4/93.4 |
| Comparative Example 2 | 55 | 106 | 190 | 650 | 53 | 62.8/93.5 |
| Comparative Example 3 | 55 | 382 | 190 | 100 | 43 | 62.1/92.8 |
| Comparative Example 4 | 55 | 139 | 210 | 550 | 48 | 62.9/93.1 |
| Comparative Example 5 | 55 | 726 | 190 | 160 | Not spray-dryable | — |

The present application claims the priority based on Japanese Patent Application filed on Feb. 28, 2020 (Japanese Patent Application No. 2020-033203), the content of which is incorporated herein by reference.

The invention claimed is:

1. A catalyst for production of carboxylic acid ester, comprising:
catalyst metal particles; and
a support supporting the catalyst metal particles,
wherein the catalyst has a hollow particle ratio of 40% or less, and
wherein the catalyst metal particles are composite particles comprising:
oxidized nickel and/or cobalt, and
X, wherein X represents at least one element selected from the group consisting of nickel, palladium, platinum, ruthenium, gold, silver, and copper.

2. The catalyst for production of carboxylic acid ester according to claim 1, wherein the hollow particle ratio is 35% or less.

3. The catalyst for production of carboxylic acid ester according to claim 1, wherein a content of the support is from 80.0 to 99.9% by mass with respect to the catalyst for production of carboxylic acid ester.

4. The catalyst for production of carboxylic acid ester according to claim 1, wherein a compositional ratio between nickel or cobalt and X in the composite particles, in terms of a Ni/(Ni+X) atomic ratio or a Co/(Co+X) atomic ratio, is from 0.20 to 0.99.

5. The catalyst for production of carboxylic acid ester according to claim 1, wherein the composite particles comprise oxidized nickel and gold.

6. The catalyst for production of carboxylic acid ester according to claim 1, wherein the support comprises silica and alumina.

7. The catalyst for production of carboxylic acid ester according to claim 1, wherein the support further comprises an oxide of at least one basic metal component selected from the group consisting of an alkali metal, an alkaline earth metal, and a rare earth metal.

8. The catalyst for production of carboxylic acid ester according to claim 1, wherein the support comprises silica, alumina, and magnesia.

9. A method for producing the catalyst for production of carboxylic acid ester according to claim 1, the method comprising:
a step (A) of preparing a support precursor slurry comprising raw material for the support at a stirring rotational speed of 120 rpm or more and 600 rpm or less, the slurry being at a temperature of 5° C. or more and 60° C. or less and having a viscosity of 10 cp or more and 550 cp or less,
a step (B) of supplying the support precursor slurry to a spray dryer to spray-dry the support precursor slurry at an inlet temperature of the spray dryer of 150° C. or more and 215° C. or less,
a step (C) of calcining after the step (B) to obtain a support, and
a step (D) of allowing the support to support the catalyst metal particles.

10. The method for producing a catalyst for production of carboxylic acid ester according to claim 9, wherein a spray drying apparatus having an inner diameter of 1000 mm or more is employed in the step (B).

11. A method for producing carboxylic acid ester comprising a step of reacting (a) an aldehyde and an alcohol or (b) one or two or more alcohols in a presence of the catalyst for production of carboxylic acid ester according to claim 1 and oxygen.

12. The method for producing carboxylic acid ester according to claim 11, wherein the aldehyde is acrolein and/or methacrolein.

13. The method for producing carboxylic acid ester according to claim 11, wherein the aldehyde is acrolein and/or methacrolein, and the alcohol is methanol.

14. The catalyst for production of carboxylic acid ester according to claim 1, wherein the catalyst comprises a supported layer, the supported layer comprising a region of the support where the composite particles are concentrated, and wherein the supported layer is present in a region extending from a surface of the catalyst to 40% of an equivalent diameter of the catalyst.

15. The catalyst for production of carboxylic acid ester according to claim 1, wherein the composite particles comprise cobalt.

* * * * *